United States Patent
Kuchenbauer et al.

(10) Patent No.: US 8,716,255 B2
(45) Date of Patent: May 6, 2014

(54) MICRORNA COMPOSITIONS AND METHODS FOR THE TREATMENT OF MYELOGENOUS LEUKEMIA

(75) Inventors: Florian Kuchenbauer, Ulm (DE); Michael Heuser, Hannover (DE); Richard Keith Humphries, Vancouver (CA)

(73) Assignee: British Columbia Cancer Agency Branch (CA)

( * ) Notice: Subject to any disclaimer, the term of this patent is extended or adjusted under 35 U.S.C. 154(b) by 526 days.

(21) Appl. No.: 12/672,715

(22) PCT Filed: Aug. 11, 2008

(86) PCT No.: PCT/CA2008/001451
§ 371 (c)(1),
(2), (4) Date: Jun. 24, 2011

(87) PCT Pub. No.: WO2009/021325
PCT Pub. Date: Feb. 19, 2009

(65) Prior Publication Data
US 2011/0244024 A1    Oct. 6, 2011

Related U.S. Application Data

(60) Provisional application No. 60/955,118, filed on Aug. 10, 2007.

(51) Int. Cl.
*A61K 31/70*    (2006.01)
*C07H 21/02*    (2006.01)
*C07H 21/04*    (2006.01)
*C12Q 1/68*    (2006.01)

(52) U.S. Cl.
USPC ......... 514/44 A; 435/375; 435/377; 536/23.1; 536/24.1; 536/24.5

(58) Field of Classification Search
None
See application file for complete search history.

(56) References Cited

U.S. PATENT DOCUMENTS

| | | |
|---|---|---|
| 5,705,385 A | 1/1998 | Bally et al. |
| 5,965,542 A | 10/1999 | Wasan et al. |
| 5,976,567 A | 11/1999 | Wheeler et al. |
| 6,287,591 B1 | 9/2001 | Semple et al. |
| 6,534,484 B1 | 3/2003 | Wheeler et al. |
| 6,586,410 B1 | 7/2003 | Wheeler et al. |
| 6,815,432 B2 | 11/2004 | Wheeler et al. |
| 7,101,995 B2 | 9/2006 | Lewis et al. |
| 7,220,400 B2 | 5/2007 | Monahan et al. |
| 7,232,806 B2 | 6/2007 | Tuschl et al. |
| 2005/0008617 A1 | 1/2005 | Chen et al. |
| 2005/0008689 A1 | 1/2005 | Semple et al. |
| 2005/0014962 A1 | 1/2005 | Gebeyehu et al. |
| 2005/0064595 A1 | 3/2005 | MacLachlan et al. |
| 2006/0008910 A1 | 1/2006 | MacLachlan et al. |
| 2006/0051405 A1 | 3/2006 | MacLachlan et al. |
| 2006/0083780 A1 | 4/2006 | Heyes et al. |
| 2007/0172950 A1 | 7/2007 | Wheeler et al. |
| 2007/0173476 A1 | 7/2007 | Leake et al. |

FOREIGN PATENT DOCUMENTS

| | | |
|---|---|---|
| WO | WO 2005/118806 A2 | 12/2005 |
| WO | WO 2006/137941 A2 | 12/2006 |
| WO | WO 2007/081680 A2 | 7/2007 |
| WO | WO 2007/081740 A2 | 7/2007 |
| WO | WO 2008/070082 A2 | 6/2008 |

OTHER PUBLICATIONS

F. Fazi et al., "A Minicircuitry Comprised of Micro-RNA-223 and Transcription Factors NFI-A and C/EBPalpha Regulates Human Granulopoiesis", Cell, Dec. 2, 2005, vol. 123(5), pp. 819-831.
R. Garzon et al., "MicroRNa gene expression during retinoic acid-induced differentiation of human acute promyelocytic leukemia", Oncogene, Jun. 14, 2007, vol. 26(28), pp. 4148-4157, 2007 Nature Publishing Group.
PCT International Preliminary Report on Patentability and Written Opinion of the International Searching Authority, PCT International Application No. PCT/CA2008/001451, filed Aug. 11, 2008.
PCT International Search Report dated Nov. 26, 2008, PCT International Application No. PCT/CA2008/001451, filed Aug. 11, 2008.
Abu-Zahra, H. "Treatment of acute myeloblastic leukemia in adults: remission induction with a combination of cyclophosphamide, cytarabine, and vincristine," Can. Med. Assoc. J., Dec. 9, 1972, vol. 107, pp. 1073-1078.
Aigner, Achim. "Applications of RNA interference: current state and prospects for siRNA-based strategies in vivo," Appl. Microbiol. Biotechnol., Apr. 25, 2007, pp. 9-21.
Aigner, Achim. "Delivery systems for the direct application of siRNAs to induce RNA interference (RNAi) in vivo," J. Biomed. Biotechnol., Feb. 27, 2006, vol. 2006, pp. 1-15.
Aigner A. Nonviral in vivo delivery of therapeutic small interfering RNAs. Curr Opin Mol Ther. (2007) 9:345-352.
Aigner, Achim. "Gene silencing through RNA interference (RNAi) in vivo: strategies based on the direct application of siRNAs," J. Biotechnol., 2006, vol. 124, pp. 12-25.
Allen, Theresa M. et al. "Drug delivery systems: entering the mainstream," Science, Mar. 19, 2004, vol. 303, pp. 1818-1822.
Aravin, Alexei et al. "Identification and characterization of small RNAs involved in RNA silencing," FEBS Letters, Aug. 18, 2005, vol. 579, pp. 5830-5840.
Bandres, Eva et al. "MicroRNAs as cancer players: potential clinical and biological effects," DNA Cell Biol., vol. 26, No. 5, 2007, pp. 273-282.
Bartel, David P. "MicroRNAs: genomics, biogenesis, mechanism, and function," Cell, vol. 116, Jan. 23, 2004, pp. 281-297.

(Continued)

*Primary Examiner* — Sean McGarry
(74) *Attorney, Agent, or Firm* — J.A. Lindeman & Co., PLLC

(57) ABSTRACT

The invention provides methods, uses, kits and compositions comprising a therapeutically effective amount of the microRNA miR-223 for treating myelogenous leukemia in a subject in need of such treatment. The invention further comprises methods encompassing the use of miR-223 for promoting the differentiation of a leukemia stem cell that is resistant to a differentiating agent, and a method of screening for candidate compounds capable of treating a myeloid leukemia by comparison of the therapeutic activity of the candidate compound with the therapeutic activity of miR-233.

14 Claims, 9 Drawing Sheets

(56) References Cited

OTHER PUBLICATIONS

Buechner, Thomas et al. "Treatment of AML in biological subgroups," Hematology, vol. 10, Supplement 1, 2005, pp. 281-285.
Cai, Xuezhong et al. "Human microRNAs are processed from capped, polyadenylated transcripts that can also function as mRNAs," RNA, vol. 10, 2004, pp. 1957-1966.
Calin, George A. et al. "A MicroRNA signature associated with prognosis and progression in chronic lymphocytic leukemia," N. Engl J Med, vol. 353, Oct. 27, 2005, pp. 1793-1801.
Calin, George A. et al. "Frequent deletions and down-regulation of microRNA genes miR15 and miR16 at 13q14 in chronic lymphocytic leukemia," PNAS, vol. 99, No. 24, Nov. 26, 2002, pp. 15524-15529.
Calin, George A. et al. "MicroRNA profiling reveals distinct signatures in B cell chronic lymphocytic leukemias," PNAS, vol. 101, No. 32, Aug. 10, 2004, pp. 11755-11760.
Calvo, Katherine R. et al. "Nup98-HoxA9 immortalizes myeloid progenitors, enforces expression of Hoxa9, Hoxa7 and Meis1, and alters cytokine-specific responses in a manner similar to that induced by retroviral co-expression of Hoxa9 and Meis1," Oncogene, vol. 21, 2002, pp. 247-4256.
Chen, Chang-Zheng et al. "MicroRNAs modulate hematopoietic lineage differentiation," Science, vol. 303, Jan. 2, 2004, pp. 83-86.
Chopra, Vivek S. et al. "Mir'acles in hox gene regulation," Bioessays, vol. 28, 2006, pp. 445 448.
Cimmino, Amelia et al. "miR-15 and miR-16 induce apoptosis by targeting BCL2," PNAS, vol. 102, No. 39, Sep. 27, 2005, pp. 13944-13949.
Costinean, Stefan et al. "Pre-B cell proliferation and lymphoblastic leukemia/high-grade lymphoma in Eμ-miR155 transgenic mice," PNAS, vol. 103, No. 18, May 2, 2006, pp. 7024-7029.
Debernardi, S. et al. "MicroRNA miR-181a correlates with morphological sub-class of acute myeloid leukaemia and the expression of its target genes in global genome-wide analysis," Leukemia, vol. 21, Mar. 1, 2007, pp. 912-916.
Denli, Ahmet M. et al. "Processing of primary microRNAs by the microprocessor complex," Nature, vol. 432, Nov. 2004, pp. 231-235.
Fazi F., et al., "Epigenetic Silencing of the Myelopoiesis Regulator microRNA-223 by the AML1/ETO Oncoprotein." Cancer Cell. (2007) 12(5): 457-466.
Fazi F., et al., "A Minicircuitry Comprised of MicroRNA-223 and Transcription Factors NFI-A and C/EBPalpha Regulates Human Granulopoiesis." (2005) Cell (2005) 123: 819-831.
Feuring-Buske M., et al., "Variable cytotoxicity of diphtheria toxin 388-granulocyte-macrophage colony-stimulating factor fusion protein for acute myelogenous leukemia stem cells." Exp Hematol. (2000) 28:1390-1400.
Feuring-Buske M., et al., "A Diphtheria Toxin-Interleukin 3 Fusion Protein is Cytotoxic to Primitive Acute Myeloid Leukemia Progenitors But Spares Normal Progenitors." Cancer Res. (2002) 62: 1730-1736.
Fuering-Buske M, Hogge DE. "Hoechst 33342 efflux identifies a subpopulation of cytogenetically normal CD34(+)CD38(−) progenitor cells from patients with acute myeloid leukemia." Blood. (2001)97:3882-3889.
Fukao T., et al., "An Evolutionarily Conserved Mechanism for MicroRNA-223 Expression Revealed by MicroRNA Gene Profiling." Cell (2007) 129: 617-631.
Garzon R. et al., "MicroRNA gene expression during retinoic acid-induced differentiation of human acute promyelocytic leukemia." Oncogene, (2007) 26: 4148-4157.
Georgantas R.W. 3rd, et al., "CD34+ hematopoietic stem-progenitor cell microRNA expression and function: A circuit diagram of differentiation control." Proc Natl Acad Sci U S A. (2007) 104 (8): 2750-2755.
Gilliland D.G., et al., "The Molecular Basis of Leukemia." Hematology Am Soc Hematol Educ Program, (2004) 80-97.
Guan Y., et al., "Detection, isolation and stimulation of quiescent primitive leukemia progenitor cells from patients with acute myeloid leukemia (AML)." Blood. (2003) 101 (8): 3142-3149.

He L,. et al., "MicroRNAs: small RNAs with a big role in gene regulation." Nat Rev Genet. (2004) 5:522-531.
He L., et al., "A microRNA polycistron as a potential human oncogene." Nature (2005) 435, 828-833.
Hernando E. "microRNAs and cancer: role in tumorigenesis, patient classification and therapy." Clin Tranl Oncol. (2007)9:155-160.
Heuser M., et al., "MN1 overexpression induces acute myeloid leukemia in mice and predicts ATRA resistance in patients with AML." Blood (2007)110: 1639-1647.
Hiddemann W, et al. "Priming with G-CSF in acute myeloid leukemia: preliminary data of the AMLCG," Annals of Hematology Poster Session I, Interdisciplinary Workshop, Satellite Symposium IV, (2004) 83(1) Supplement, pp. S13-S58 (p. S53).
Hiddemann W., et al., "Towards a pathogenesis-oriented therapy of acute myeloid leukemia." Crit Rev Oncol Hematol. (2005) 56: 235-245.
Heinrichs, S. and Look, A.T., "siRNA-mediated knockdown of HOXB9 and HOXA10 in an AML cell line results in a reduction of the growth rate," Interdisciplinary Workshop, Satelite Symposia I-IV, Poster Session I, AML: Clinical Observations Poster #58, (2004) 83(1) Supplement, pp. S13-S58 (p. S28).
Hogge D.E.,"The efficacy of diphtheria-growth factor fusion proteins is enhanced by co-administration of cytosine arabinoside in an immunodeficient mouse model of human acute myeloid leukemia." Leuk Res. (2004) 28:1221-1226.
Hornstein E., et al. "The microRNA miR-196 acts upstream of Hoxb8 and Shh in limb development." Nature. (2005)438: 671-674.
Heuser M., et al., "High meningioma 1 (MN1) expression as a predictor for poor outcome in acute myeloid leukemia with normal cytogenetics." Blood (2006)108: 3898-3905.
Jay, C., et al., "miRNA Profiling for Diagnosis and Prognosis of Human Cancer." DNA Cell Biol (2007) 26:283-292.
Kawasaki, H., et al. "MicroRNA-196 inhibits HOXB8 expression in myeloid differentiation of HL60 cells." Nucleic Acids Sym Ser (Oxf). (2004) 48:211-212.
Kim, V.N. "MicroRNA biogenesis: coordinated cropping and dicing." Nat Rev Mol Cell Biol (2005) 6: 376-385.
Koldehoff, M., et al. "Therapeutic application of small interfering RNA directed against bcr-abl transcripts to a patient with imatinib-resistant chronic myeloid leukaemia." Clin Exp Med. (2007) 7:47-55.
Koschmieder, S., et al. "Role of Transcription Factors C/EBPalpha and PU.1 in Normal Hematopoiesis and Leukemia." Int J Hematol (2005) 81:368-377.
Kuchenbauer, F., et al., "AML1-ETO Needs a Partner: New Insights into the Pathogenesis of t(8;21) Leukemia." Cell Cycle. (2005) 4(12): 1716-1718.
Kuchenbauer, F., et al. "Impact of FLT3 mutations and promyelocytic leukaemia-breakpoint on clinical characteristics and prognosis in acute promyelocytic leukaemia." Br J Haematol (2005) 130:196-202.
Landgraf, P., et al. "A Mammalian microRNA Expression Atlas Based on Small RNA Library Sequencing." Cell. (2007) 129: 1401-1414.
Lewis, B.P., et al. "Conserved Seed Pairing, Often Flanked by Adenosines, Indicates that Thousands of Human Genes are MicroRNA targets." Cell (2005) 120: 15-20.
Looijenga, L.H., et al. "Relevance of microRNAs in normal and malignant development, including human testicular germ cell tumours." Int J Androl. (2007) 4: 304-314.
Lu, J., et al. "MicroRNA expression profiles classify human cancers." Nature (2005) 435: 834-838.
Lui, W.O., et al. "Patterns of Known and Novel Small RNAs in Human Cervical Cancer." Cancer Res. (2007) 67: 6031-6043.
Lund, E., et al. "Nuclear Export of MicroRNA Precursors." Science. (2004) 303: 95-98.
Ma, L., et al. "Tumour invasion and metastasis initiated by microRNA-10b in breast cancer." Nature. (2007) 449: 682-688.
Moore, M.A.S. et al. "NUP98 Dysregulation in Myeloid Leukemogenesis." Ann NY Acad Sci. (2007) 1106: 114-142.
Negrini, M., et al. "MicroRNAs in human cancer: from research to therapy." J Cell Sci. (2007) 120: 1833-1840.
Nervi C, Fazi F, Rosa A, Fatica A, Bozzoni I. Emerging Role for microRNAs in acute promyelocytic leukemia. Curr Top Microbiol Immunol. 2007;313:73-84.

(56) References Cited

OTHER PUBLICATIONS

O'Toole, A.S., et al. "Comprehensive thermodynamic analysis of 3' double-nucleotide overhangs neighboring Watson-Crick terminal base pairs." Nucleic Acids Red. (2006) 34: 3338-3344.

Pai, S.I., et al. "Prospects of RNA interference therapy for cancer." Gene Ther. (2006) 13: 464-477.

Park, J.K., et al. "The miRNA Pathway Intrinsically Controls Self-Renewal of *Drosophila* Germline Stem Cells." Curr Biol. (2007) 17: 533-538.

PCT International Search Report of International Application No. PCT/CA2008/001451 mailed Nov. 26, 2008.

PCT International Preliminary Report on Patentability of International Application No. PCT/CA2008/001451 mailed Feb. 25, 2010.

Pineault N., et al. "Transplantable cell lines generated with NUP98-Hox fusion genes undergo leukemia progression by Meis1 independent of its binding to DNA." Leukemia. (2005) 19: 636-643.

Pineault N., et al. "Differential and Common Leukemogenic Potentials of Multiple NUP98-Hox Fusion Proteins Alone or with Meis1." Mol Cell Biol. (2004) 24: 1907-1917.

Pineault N, et al. "Induction of acute myeloid leukemia in mice by the human leukemia-specific fusion gene NUP98-HOXD13 in concert with Meis1." Blood. (2003) 101: 4529-4538.

Porkka, K.P., et al. "MicroRNA Expression Profiling in Prostate Cancer." Cancer Res. (2007) 67: 6130-6135.

Ramkissoon, S.H., et al. "Hematopoietic-specific microRNA expression in human cells." Leuk Res. (2006) 5:643-647.

Rice, K.L., et al. "HOX deregulation in acute myeloid leukemia." J Clin Invest. (2007) 117:865-868.

Ro, S., et al. "Tissue-dependent paired expression of miRNAs." Nucleic Acids Res. (2007) 35(17):5944-5953.

Ruby, J.G., et al. "Large-Scale Sequencing Reveals 21U-RNAs and Additional MicroRNAs and Endogenous siRNAs in *C. elegans*." Cell (2006) 127:1193-1207.

Scherr, M., et al. "Specific inhibition of bcr-abl gene expression by small interfering RNA." Blood. (2003) 101:1566-1569.

Sevignani, C., et al. "MicroRNA genes are frequently located near mouse cancer susceptibility loci." Proc Natl Acad Sci U S A. (2007) 104:8017-8022.

Shell, S., et al. "Let-7 expression defines two differentiation stages of cancer." Proc Natl Acad Sci U S A. (2007) 104:11400-11405.

Somervaille, T.C., et al. "Identification and characterization of leukemia stem cells in murine MLL-AF9 acute myeloid leukemia." Cancer Cell. (2006) 10:257-268.

Sugatani, T., et al. "MicroRNA-223 is a Key Factor in Osteoclast Differentiation." J Cell Biochem. (2007) 101:996-999.

Tang, F., et al. "Maternal microRNAs are essential for mouse zygotic development." Genes Dev. (2007) 21:644-648.

Tenen, D.G. "Disruption of differentiation in human cancer: AML shows the way." Nat Rev Cancer. (2003) 3:89-101.

Thatcher, E.J., et al. "miRNA Expression Analysis During Normal Zebrafish Development and Following Inhibition of the Hedgehog and Notch Signalling Pathways." Dev Dyn. (2007) 236:2172-2180.

Tran, N., et al. "MicroRNA expression profiles in head and neck cancer cell lines." Biochem Biophys Res Commun. (2007) 358:12-17.

Wang, Y., et al. "DGCR8 is essential for microRNA biogenesis and silencing of embryonic stem cell self-renewal." Nat Genet.(2007) 39:380-385.

Wilson, K.D., et al. "Effects of intravenous and subcutaneous administration on the pharmacokinetics, biodistribution, cellular uptake and immunostimulatory activity of CpG ODN encapsulated in liposomal nanoparticles." Int Immunopharmacol. (2007) 7:1064-1075.

Yalcintepe, L., et al. "Expression of interleukin-3 receptor subunits on defined subpopulations of acute myeloid leukemia blasts predicts the cytotoxicity of diphtheria toxin interleukin-3 fusion protein against malignant progenitors that engraft in immunodeficient mice." Blood. (2006) 108:3530-3537.

Yu SL, Chen HY, Yang PC, Chen JJ. Unique MicroRNA signature and clinical outcome of cancers. DNA Cell Biol. 2007;26:283-292.

MICRORNA COMPOSITIONS AND METHODS FOR THE TREATMENT OF MYELOGENOUS LEUKEMIA

FIELD OF INVENTION

The present invention provides compositions and methods for the treatment of myelogenous leukemia. More specifically, the present invention provides miR-223 compositions and methods for the treatment of myelogenous leukemia.

BACKGROUND OF THE INVENTION

Leukemias encompass hematological malignancies, characterized by the clonal expansion of hematopoietic cells exhibiting abnormal proliferation, blocked differentiation, and reduced apoptosis. Leukemias are generally categorized into multiples types, such as acute or chronic, or myeloid or lymphoid, depending on the rate of disease progression and hematopoietic lineage, with further classification into subtypes based on the stage of differentiation blockage.

Chronic myelogenous leukemia (CML) is also known as chronic myeloid leukemia, chronic myelocytic leukemia, or chronic granulocytic leukemia. The majority of patients diagnosed with CML have a characteristic chromosomal abnormality called the Philadelphia chromosome which results in the formation of the BCR-ABL fusion protein. CML generally progresses through three phases characterized by the number of immature leukemic cells in the blood and bone marrow of the patient. Traditional therapies for CML include chemotherapy, bone marrow transplantation, and interferon therapy, although targeted therapies are under development.

Acute myelogenous leukemia (AML), also known as acute myeloid leukemia, acute myelocytic leukemia, acute granulocytic leukemia, and acute non-lymphocytic leukemia, is characterized by abnormal proliferation of myeloid cells. The development of AML is thought to be mediated by two major mechanisms: increased self-renewal and a block in differentiation of the leukemia cells (Gilliland et al. 2004), in contrast to differentiation in normal hematopoiesis, which is mediated by lineage specific transcription factors (e.g. CEBPα, PU-1) directing the hematopoietic stem cells to differentiate into progenitor cells and finally to mature blood cells (Koschmieder et al. 2005). AML blasts, reflecting the immature, accumulating leukemia cells, can display a block in differentiation at any maturation level.

Standard treatment of AML to date includes intensive chemotherapy and bone marrow transplantation (Hiddemann et al. 2005). The overall long-term survival rate for AML patients is between 20-30%, depending on the treatment regime and study (Buechner et al. 2005). As chemotherapy is not a targeted therapy, AML patients often suffer from side-effects and relapse of the disease. The current standard chemotherapy for AML is a 30 year old treatment regime with cytarabine and an anthracycline, which is cytotoxic and has other deleterious side effects. Despite emerging novel targeted therapies like FLT3 inhibitors and anti-CD33 antibodies, only the introduction of all-trans-retinoic-acid (ATRA) for acute promyelocytic leukemia (also known as APL or AML M3) has provided a differentiating treatment for leukemia cells. The use of ATRA combined with chemotherapy has increased long term survival to 80-90% in APL patients (Kuchenbauer et al. 2005). However, many AML patients are resistant to exogenous differentiating agents, including ATRA (Hiddemann et al. 2004).

Micro RNAs (miRNAs) are generally 21-24 nucleotide (nt) long RNA molecules and are thought to be important posttranscriptional regulators of mRNAs (Bartel 2004). mRNAs are initially transcribed as longer RNA molecules called primary-miRNAs (pri-miRNAs), but undergo a multi-step maturation process involving cleavage through Drosha (nuclear) and Dicer (cytoplasmic) (Kim 2005). The resulting double stranded RNA molecule, consisting of the mature miRNA strand and its partially complementary strand counterpart miRNA star (miRNA*), enters a protein complex named RNA induced silencing complex (RISC) that uses the strand with the mature miRNA sequence as template for degradation of the specific, complementary mRNA (Kim 2005). The mature miRNA is characterized by a "seed region", generally comprising the bases 2-7 of the 5' end (Lewis et al. 2005). The seed region is thought to primarily define the specificity of a miRNA towards the 3'UTR of its target mRNAs and has been used for computational target predictions (Lewis et al. 2005). For each miRNA a few hundred target mRNAs are predicted, whereas relatively few targets have been experimentally validated to date. Recent deep sequencing approaches led to changes in the current miRNA databases and implicate miRNA* as an active miRNA molecule (Ruby et al. 2006). Furthermore, in some miRNA stemloops, such as mir-302b, both the 5' and the 3' stemloop sequences are annotated as mature miRNAs, suggesting that both miRNA strands can have functional properties.

In general, miRNAs are closely related to siRNAs, which are double-stranded RNA molecules that are also processed by Dicer. In contrast to primitive organisms like C. elegans, endogenous siRNAs rarely occur in mammals and consequently do not play a physiological role (Aravin and Tuschl 2005).

A connection between miRNAs and hematopoiesis was made when it was demonstrated that certain miRNAs are expressed within specific hematopoietic lineages and that their expression levels regulate hematopoietic differentiation (Chen et al. 2004). MicroRNA profiling in chronic lymphatic leukaemia and other lymphomas suggests that miRNA expression changes during pathogenesis and implied that miRNAs may play a functional role in hematopoietic disorders. Overexpression of miR-155 and the miR-17-19b cluster was implicated in promoting the development of lymphomas, suggesting that miRNAs can act as oncogenes (Costinean et al. 2006; He et al. 2005).

Relatively little is known about the role of miRNAs in leukemias of myeloid origin. A study correlating the expression levels of 5 miRNAs with the genome-wide mRNA expression profiles of the same leukemias suggested that miR-181a correlates strongly with the AML morphological sub-type and with the expression of genes previously identified through sequence analysis as potential interaction targets (Debernadi et al. 2007). Another study suggested that expression of miR-223 induces granulocytic differentiation in an acute promyelocyte leukemia (APL) model and is controlled by a regulatory circuitry involving miR-223 and two transcriptional factors, NFI-A and CEBPalpha (Fazi et al. 2005). It has been also reported that miR-223 expression underlies a highly conserved transcriptional mechanism involving the myeloid transcription factors PU-1 and CEBPalpha (Fukao et al. 2007).

SUMMARY OF THE INVENTION

The invention provides, in part, compositions and methods for treating myeloid leukemias, including acute myeloid leukemia (AML) and chronic myeloid leukemia (CML), in a subject in need thereof, by administering an effective amount of a miR-223 molecule.

In one aspect, the invention provides a method of treating a myeloid leukemia (e.g., chronic myeloid leukemia (CML) or acute myeloid leukemia (AML))by administering an effective amount of a miR-223 molecule to a subject in need thereof In an alternative aspect, the invention provides use of a miR-223 molecule for treating a myeloid leukemia. The leukemia may be resistant to a differentiating agent, such as a retinoic acid (e.g., all-trans-retinoic acid (ATRA)) or a cytokine (granulocyte colony stimulating factor (G-CSF) or granulocyte macrophage colony stimulating factor (GM-CSF). The AML maybe a non-acute promyelocytic leukemia (non-APL AML) or maybe an ATRA-resistant APL. The miR-223 molecule may include a sequence that is substantially identical to a sequence selected from one or more of SEQ ID NOs: 1-20. The treating may include promoting differentiation in a leukemic cell.

In alternative embodiments, the treating or the use may further include administering or providing a chemotherapeutic agent, or may include stem cell transplantation. The chemotherapeutic agent may be administered or provided or the stem cell transplantation may be performed prior to or after administration or provision of the miR-223 molecule. The miR-223 molecule may be administered as part of a consolidation (post-remission therapy).

The subject may have relapsed leukemia or may be at a high risk for relapse. The subject may be a poor candidate for high dose chemotherapy. The subject may be over 60 years of age. The subject may be a poor candidate for chemotherapy or for stem cell transplantation. The subject may be a human. In an alternative aspect, the invention provides a method for promoting the differentiation of a leukemic stem cell that is resistant to a differentiating agent, the method comprising administering a miR-223 molecule to the leukemic stem cell. The leukemic stem cell may be a CML cell or an AML cell. The differentiating agent may be a retinoic acid (e,g., ATRA) or a cytokine (e.g., G-CSF or GM-CSF). The AML may be a non-acute promyelocytic leukemia (non-APL AML) or may be an ATRA-resistant APL. The miR-223 molecule may include a sequence that is substantially identical to a sequence selected from one or more of SEQ ID N0s: 1-20. The leukemic cell may be a CD34+, CD38- cell.

In an alternative aspect, the invention provides a pharmaceutical composition comprising a miR-223 molecule in combination with a pharmaceutical carrier. The miR-223 molecule may include a sequence that is substantially identical to a sequence selected from one or more of SEQ ID NOs: 1-20. The leukemic cell may be a CD34+, CD38- cell. The composition is provided may be provided in a liposomal particle, e.g., a nanoparticle.

In an alternative aspect, the invention provides a kit comprising the pharmaceutical composition together with instructions for use in treating a myeloid leukemia.

In an alternative aspect, the invention provides a method for screening for a candidate compound for treating a myeloid leukemia, the method by: providing a test compound; providing a miR-223 molecule; c) determining the ability of the test compound to promote differentiation of a leukemic stem cell or treat leukemia in an animal model; d) determining the ability of the miR-223 molecule to promote differentiation of a leukemic stem cell or treat leukemia in an animal model; and comparing the ability of the miR-223 molecule and test compound to promote differentiation of a leukemic stem cell or treat leukemia in an animal model, where the test compound is a candidate compound if the test compound is capable of promoting differentiation of a leukemic stem cell or treating leukemia in an animal model equivalent to or better than the miR-223 molecule. In some embodiments, the screening method need not perform the step of determining the ability of the miR-223 molecule to promote differentiation of a leukemic stem cell or treat leukemia in an animal model but may rely on prior established references or standards.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 6 shows a sequence alignment of miR-223 precursor sequences from various species (SEQ ID NOs: 1 and 6-20). The human sequence is depicted by the box. The shaded sections indicate areas of sequence identity, with the light shaded sections indicating areas of total identity across the species listed.

DETAILED DESCRIPTION

Figure 1A:
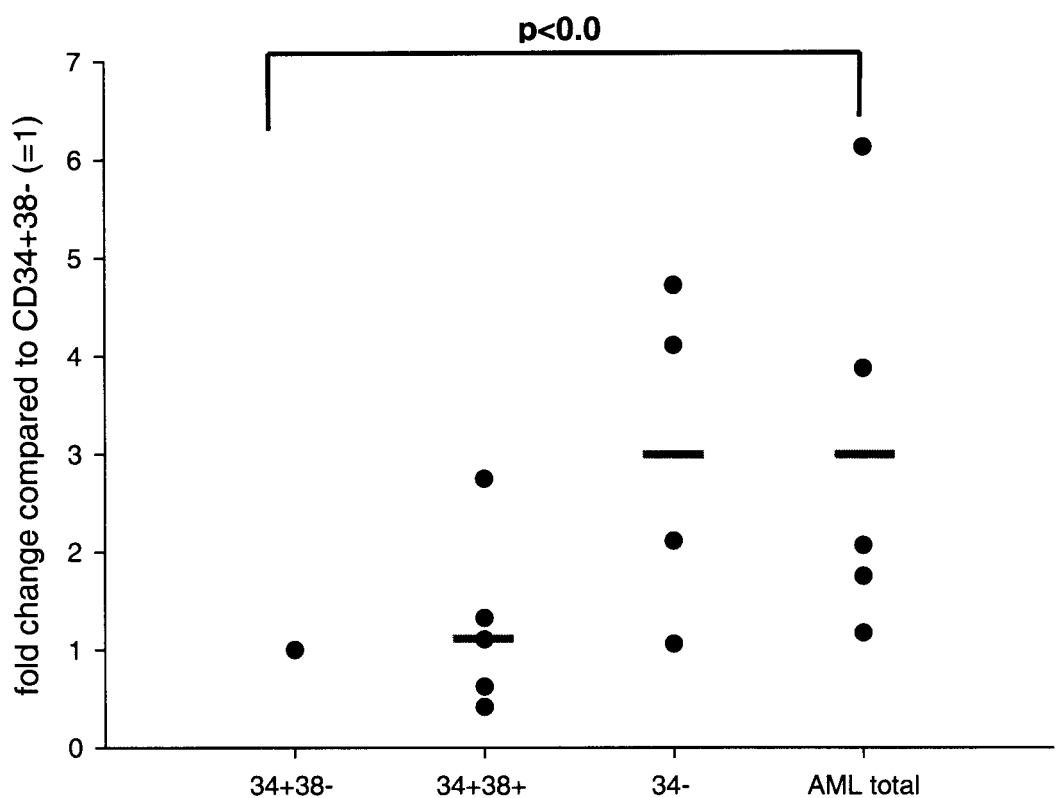
FIG. 1A shows the relative expression of mature miR-223 in 5 randomly chosen AML patient samples sorted into 4 subgroups ranging from primitive CD34+38- to more differentiated CD34- cell populations. The AML stem cell containing CD34+38- subgroup showed a significantly lower expression of miR-223.

The invention provides, in part, compositions and methods for treating myeloid leukemias, including acute myeloid leukemia (AML) and chronic myeloid leukemia (CML), in a subject in need thereof, by administering an effective amount of a miR-223 molecule.

Hematopoietic Cells

By "hemopoietic" or "hematopoietic" is meant blood or blood cells formed by hematopoiesis or hemopoiesis in bone marrow and peripheral blood.

Hematopoietic Stem Cells (HSCs) are the most primitive cells present in the blood system and are capable of generating all of the cell populations present in the blood. HSCs are also capable of virtually indefinite self-renewal (i.e., remaining a stem cell after cell division), and have the ability to choose between self-renewal and differentiation (ultimately, into a mature hematopoietic cell). HSCs also migrate in a regulated fashion, and are subject to regulation by apoptosis. HSCs are rare and are thought to account for an estimated 1 in 10,000 to 15,000 nucleated cells in the bone marrow, and an estimated 1 in 100,000 in the peripheral blood.

Hematopoietic Progenitor Cells (HPCs) are cells that are derived from and further differentiated from HSCs. When compared to HSCs, HPCs have a relatively reduced capacity to differentiate (they can generate only a subset of the possible lineages), although they are capable of extensive and rapid proliferation and can typically generate a large number of mature cells. Importantly, HPCs have a limited capacity to self-renew and therefore require regeneration from HSCs. A subset of HPCs can be held in a "pool" i.e., where the cells are not actively cycling. HPCs are generally present in larger numbers than HSCs and can therefore be more rapidly mobilized or expanded in the hematopoietic recovery process. HPCs include Common Lymphoid Progenitors (CLPs), which in adults, have the potential to generate all of the lymphoid but not the myeloerythroid cells, and Common Myeloid Progenitors (CMPs), which have the potential to generate all of the mature myeloerythroid cells, but not lymphoid cells.

HPCs give rise to the different blood cell types of the myeloid and lymphoid lineages. The myeloerythroid lineage includes granulocytes (neutrophils, eosinophils, basophils), mast cells, monocytes (histiocytes, macrophages, dendritic cells, Langerhans cells, microglia, Kupffer cells, osteoclasts), megakaryoblasts, megakaryocytes, erythrocytes, platelets and their various progenitors, eg., colony forming units of the granulocytic/monocytic lineage (CFU-GM), burst forming units of the erythroid lineage (BFU-E), etc. The lymphoid lineage includes T-cells, B-cells, NK-cells and their progenitors, etc.

HSCs and/or HPCs may be obtained from bone marrow, or from peripheral blood upon pre-treatment with cytokines, such as granulocyte colony stimulating factor (G-CSF), which induces release of HSCs and/or HPCs from the bone marrow. HSCs and/or HPCs may also be obtained from umbilical cord blood, placenta, fetal liver or spleen, etc. Markers specific for HSCs and/or HPCs are known in the art, as are assays for detecting and isolating HSCs and/or HPCs and more differentiated hemopoietic cells.

Mature hematopoietic cells are terminally differentiated cells and include neutrophils, eosinophils, basophils, histiocytes, macrophages, dendritic cells, langerhans cells, microglia, Kupffer cells, osteoclasts, erythrocytes, platelets, T-cells, B-cells, and NK-cells.

Myelogenous Leukemias

Myelogenous or myeloid leukemias are those that result from the aberrant proliferation or development of myeloid cells.

"Chronic myelogenous leukemia" or "CML" is also known as chronic myeloid leukemia, chronic myelocytic leukemia, or chronic granulocytic leukemia. The majority of patients diagnosed with CML have a characteristic chromosomal abnormality called the Philadelphia chromosome which results in the formation of the BCR-ABL fusion protein. CML generally progresses through three phases characterized by the number of immature leukemic cells (blasts) in the blood and bone marrow of the patient. In the first phase, termed the chronic phase, the number of blasts in the blood and bone marrow is generally less than 5%. The second phase, known as the accelerated phase, is evidenced by an increase in the number of blasts to about 15% and can last weeks to months. The third phase or the "blast crisis" occurs when more than 30% of the cells are blasts, which may metastasize and form tumors in the bone or lymph nodes, and at which point the chronic leukemia is considered to have transformed into an aggressive acute leukemia. Traditional therapies for CML include chemotherapy, bone marrow transplantation, and interferon therapy. Emerging therapies for CML include targeted therapies such as peptide vaccines (e.g., to BCR-ABL).

"Acute myelogenous leukemia" or AML is also commonly known as acute myeloid leukemia, acute myelocytic leukemia, acute granulocytic leukemia, and acute non-lymphocytic leukemia. AML is generally characterized by abnormal proliferation of myeloid cells. AML may be mediated by two major mechanisms: increased self-renewal and a block in differentiation of the leukemia cells, which results in accumulation of immature cells. AML myeloblasts, reflecting the relatively immature, accumulating leukemia cells (e.g., compared to mature hematopoietic cells), may display a block in differentiation at any maturation level.

AML can be classified into subtypes based on morphology, cytochemistry, immunological markers and/or cytogenetics. Common classification systems include the French-American-British (FAB) classification which divides AML into 8 subtypes, M0 through M7, based on differentiation of the malignant leukemia cells, and the World Health Organization (WHO) classification which contains additional descriptive information on AML subtypes.

Existing or proposed treatments for AML include chemotherapy, bone marrow transplantation, and FLT3 inhibitors and anti-CD33 antibodies. For example, chemotherapy using cytarabine (ara-C) alone or in combination with an anthracycline (e.g., daunorubicin or idarubicin) is used. Such chemotherapeutic regimes may however exhibit deleterious side effects, such as myelosuppression, increased risk of infection and are frequently associated with relapse. Consolidation (post-remission) therapies for AML may include additional intensive chemotherapy for patients with a good prognosis, or may include bone marrow transplantation, such as allogeneic stem cell transplantation, for patients who have a high risk for relapse, are able to tolerate a transplant, and have a suitable donor. Patients with relapsed AML who are not good candidates for high-dose chemotherapy and are over 60 years have been approved for treatment with the monoclonal antibody-linked cytotoxic agent gemtuzymab ozogamicin (Mylotarg™) in the United States.

"Acute Promyelocytic Leukemia" (APL) is a subtype of AML characterized by the expansion of malignant myeloid cells blocked at the promyelocyte stage of differentiation. APL is classified as the M3 subtype of AML (AML M3) under the FAB classification system, and is associated with chromosomal translocations affecting the retinoic acid receptor alpha (RARalpha) gene on chromosome 17q21. Known treatments for APL include all-trans-retinoic-acid (ATRA). Arsenic trioxide has been approved in the United States for treatment of patients with relapsed APL.

APL is well-characterized at the molecular level, whereas other types of AML (non-APL AML) are heterogeneous and involve different molecular events leading to blocked, ATRA- or other differentiating agent insensitive myeloid differentiation. However, APL subforms that are ATRA insensitive are known.

A "leukemic stem cell" (LSC), as used herein, refers to a cell that sustains the disease and promotes the expansion of a leukemic clone, which blocks and outgrows normal hematopoiesis. An LSC therefore refers to a cell having extensive self-renewal and limited differentiation abilities. In general, an LSC represents only about 0.2-1% of the totality (bulk) of leukemic cells e.g., AML cells. In human patients, it is suggested that LSCs are the cells responsible for resistance to chemotherapy and give rise to the relapses in leukemia after apparent remission. An LSC is capable of transferring a myeloid leukemia e.g., AML, from a human patient when implanted into immunodeficient mice, in contrast to non-LSC leukemic cells which are not capable of causing a myeloid leukemia when implanted into immunodeficient mice. In alternative embodiments, an LSC may be committed to the myeloid lineage. In alternative embodiments, an LSC may be distinguished from a non-LSC leukemic cell e.g., a leukemic progenitor cell (LPC). In alternative embodiments, an LSC may exhibit limited differentiation into an LPC. In alternative embodiments, an LSC may be incapable of giving rise to a daughter cell that is more differentiated than the parent LSC.

LSC can be enriched or isolated by using specific antibody combinations. and functionally determined by using murine xenograft models e.g. NOD/SCID mice. In alternative embodiments, an LSC includes a CD34+, CD38− cell. In alternative embodiments, an LSC includes phenotypic markers including one or more of B220 or IL3R. In alternative embodiments, an LSC does not exhibit phenotypic markers such as one or more of CD90, CD 117, CD 123 or c-Kit. In alternative embodiments, an LSC is sensitive to parthenolide or TDZD-8 (4-Benzyl-2-methyl-1,2,4-thiadiazolidine-3,5-dione) when compared to an HSC. In alternative embodiments, an LSC exhibits activation of NF-kappaB. In alternative embodiments, an LSC is not a committed leukemic progenitor cell. Additional properties of LSCs are known in the art.

In alternative embodiments an LSC may be an AML LSC. In alternative embodiments, an LSC may be a non-APL LSC e.g., of the M0, M1, M2, M4 or M5 AML subtypes (based on the FAB system) and/or may be one or more of CD34+, CD38−, CD71−, CD90−, HLA-DR−, CD117−, and/or CD123+, etc. In alternative embodiments, an LSC may be a CML LSC.

By "promoting differentiation" or "promotion of differentiation" is meant one or more of overcoming a block in differentiation, or increasing differentiation, or decreasing the self-renewal of a leukemic cell, e.g., an LSC or LPC. In alternative embodiments, promoting differentiation may include increasing cell death e.g., apoptosis. It is to be understood that the promotion of differentiation may be partial, as long as there is a detectable difference when compared with a control or reference. The promotion of differentiation may be a change (increase or decrease) of any integer value between 10% and 90%, e.g., 10%, 20%, 30%, 40%, 50%, 60%, 70%, 80%, 90%, or may be over 100%, such as 200%, 300%, 500% or more, when compared with a control or reference subject, sample or compound. By "self-renewal" is meant the ability to maintain stem cell-like (e.g. LSC-like) characteristics after cell division or to maintain the characteristics of the parent cell. By "differentiation" is meant the ability to give rise to committed progenitors.

Animal Models of Myeloid Leukemias

MN1 and NUP98-HOXD13 (ND13)+Meis1[14-17] are two clinically relevant AML animal models.

MN1 gene overexpression has been implicated as a predictor for poor clinical outcome in AML patients with normal cytogenetics[18] and predicts resistance to the differentiating effect of ATRA[14]. The MN1 model disturbs retinoic acid signaling, as do various models of acute promyelocytic leukemia (Heuser et al. 2007; Heuser et al. 2006). However, MN1 is sufficient to induce leukemia in mice by itself in contrast to APL, ATRA resistance is much higher than in APL (clinically ATRA resistant vs. clinically ATRA sensitive) and, on a molecular level, RARalpha is not truncated or fused to another protein as seen in APL.

Another frequently found phenomenon in non-APL AML is aberrant HOX gene expression[19]. HOX genes are also frequent partners in NUP98 translocations, which comprise up to 5% of translocations found in leukemias[19], leading to aberrant HOX gene expression.

Both AML models immortalize bone marrow cells in vitro and cause highly lethal leukemias in mice with a median survival of 30-60 days after intravenous injection[14,15,17]. Furthermore, MN1 and ND13Meis1 cells are characterized by a block on different maturation levels. ND13+Meis1 cells display an arrest on the myeloid progenitor level, whereas MN1 cells exhibit a more primitive phenotype. In addition, MN1 and ND13+Meis1 cells show a downregulation of the myeloid transcription factor and miR-223 regulator CEPBalpha compared to normal bone marrow.

Other animal models of AML include, without limitation, HOXA9, CDX2, AML–ETO+FLT3, NUP98–HOXA9 and MLL–AF9.

Animal models of CML include, without limitation, BCR-ABL.

MiR-223

MiR-223 is a myeloid-specific miRNA expressed in differentiating myeloid cells. MiR-223 is highly expressed in non-leukemic cells (e.g., normal hematopoietic cells) and relatively poorly expressed in leukemic cells. For example, pre-miR-223 is highly expressed in the myeloid progenitor ND13 cells, but is drastically downregulated in the leukemic ND13+Meis1 cells. In alternative embodiments, miR-223 is highly expressed in differentiated leukemic cells and relatively poorly expressed in leukemic stem cells.

A "miR-223 molecule" includes a processed or unprocessed RNA transcript from a miRNA gene. An unprocessed miRNA transcript may also be called a miR-223 precursor or a primary miR-223, and may include an RNA molecule from about 60 to about 120 nucleotides, or about 70 to about 100 nucleotides, in length. The structure and nucleic acid sequence of a pre-miR-223, including the embedded sequences of miR-223 (highlighted light—bottom strand) and miR-223* (highlighted dark—top strand) are exemplified below.

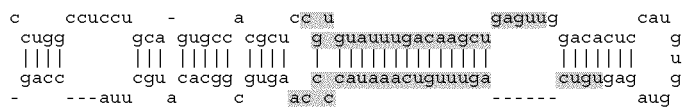

The linear sequence of exemplary pre-miR-223 molecules are as follows:
Sequence (5'→3') of human pre-miR-223:

```
                                                    (SEQ ID NO: 1)
CCUGGCCUCCUGCAGUGCCACGCUCCGUGUAUUUGACAAGCUGAGUUGGA

CACUCCAUGUGGUAGAGUGUCAGUUUGUCAAAUACCCCAAGUGCGGCACA

UGCUUACCAG
```

A miR-223 precursor molecule may be processed into smaller fragments by digestion with an RNAase, for example, Dicer. The products of a processed miR-223 precursor molecule may include "mature" miR-223 molecules of about 19 to about 25 nucleotides (or any integer therebetween), or of about 21 to about 24 nucleotides. In alternative embodiments, products of a processed miR-223 precursor molecule may include fragments that are fully or partially complementary to the mature miR-223 molecule (known as a miR-223 star (*) molecules).

The sequences of exemplary miR-223 and miR-223* molecules include the following:

```
Sequence (5' → 3') of human miR-223:
UGUCAGUUUGUCAAAUACCCCA       (SEQ ID NO: 2)

Sequence (5' → 3') of human miR-223*:
CGUGUAUUUGACAAGCUGAGUU       (SEQ ID NO: 3)
```

Exemplary "seed region" sequences (e.g., indicated as positions 2-7 of a mature miRNA molecule, Lewis et al., 2005) of the of human miR-223 and miR-223* molecules are as follows:

```
Seed region sequence (5' → 3') of miR-223:
GUCAGU              (SEQ ID NO: 4)

Seed region sequence (5' → 3') of miR-223*:
GUGUAU              (SEQ ID NO: 5)
```

Figure 6:
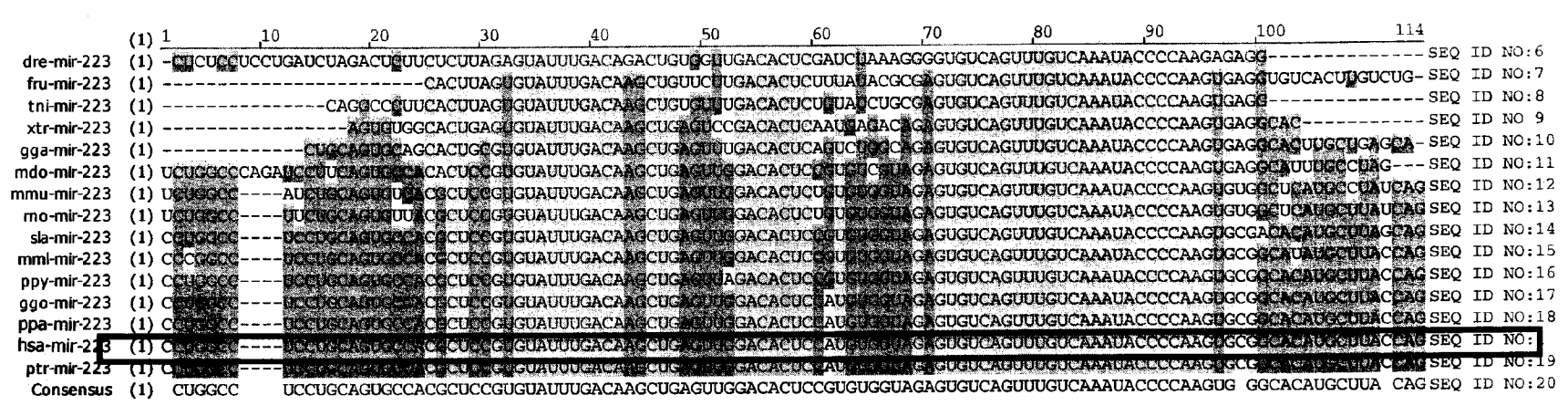

Further pre-miR-223 sequences from various species (SEQ ID NOs: 1, and 6-19) together with a consensus sequence (SEQ ID NO: 20) are provided in FIG. 6, which shows a detailed alignment of the sequences.

MiR-223 molecules according to the invention include, without limitation, single stranded molecules (e.g., pre-miR-223 molecules such as those set forth in SEQ ID NOs: 1, and 6-20; mature miR-223 molecules such as those set forth in SEQ ID NO: 2 and SEQ ID NOs: 1, and 6-19; miR-223* molecules e.g., SEQ ID NO: 3; or seed region sequences (SEQ ID NOs: 4 or 5), double stranded molecules (e.g., double stranded molecules comprising paired miR-223 and miR-223* sequences; SEQ ID NOs: 2 and 3, respectively), etc.

In alternative embodiments, miR-223 molecules include "substantially identical" sequences, for example, sequences that are substantially identical to the miR-223 molecules described herein (e.g., SEQ ID NOs: 1-20). A "substantially identical" sequence as used herein is a nucleotide sequence that differs from a miR-223 sequence or the complement thereof only by one or more substitutions located at positions of the sequence that do not destroy the biological function of the nucleic acid molecule. By "biological function" is meant promoting differentiation, or inhibiting or decreasing self-renewal or engraftment, of a leukemic cell such as an LSC or LPC, or treating a myeloid leukemia such as AML or CML. A substantially identical sequence can be any integer from 60% to 99%, or more generally at least 60%, or at least 65%, 75%, 80%, 85%, 90%, or 95%, or as much as 96%, 97%, 98%, or 99% identical when optimally aligned at the nucleotide level to the sequence used for comparison using, for example, BLASTN through miRbase (microrna[dot]sanger[dot]ac [dot]uk/sequences/search[dot]shtml). Such software matches similar sequences by assigning degrees of homology to various substitutions, deletions, substitutions, and other modifications. The length of comparison sequences may be at least 5, 6, 7, 8, 9, 10, 11, 12, 13, 14, 15, 16, 17, 18, 19, 20, 21, 22, 23, 24 or 25 nucleotides, or at least 30, 35, 40, 45, or 50 nucleotides, or any integer value therebetween. In alternate embodiments, the length of comparison sequences may be at least 55, 60, 65, 70, 75, 80, 85, 90, 95, 100, 105, 110, 115 or 120 nucleotides, or any integer value therebetween.

Alternatively, or additionally, two nucleic acid sequences may be "substantially identical" if they hybridize under high stringency conditions that allow hybridization between homologous sequences, but do not allow substantial hybridization of non-homologous sequences. In some embodiments, high stringency conditions are, for example, conditions that allow hybridization at 0.02-0.15M NaCl at temperatures of about 30° C. to about 70° C., or about 40° C. to about 60° C. Exemplary stringent hybridization conditions include 50% formamide, 5×SSC, 1% SDS at 42° C., or 5×SSC, 1% SDS at 65° C. Hybridizations may be carried out over a period of about 20 to 30 minutes, or about 2 to 6 hours, or about 10 to 15 hours, or over 24 hours or more. A common technique for hybridization of RNA molecules in Northern hybridization. The high stringency conditions used in such techniques are well known to those skilled in the art of molecular biology, and examples of them can be found, for example, in Ausubel et al., Current Protocols in Molecular Biology, John Wiley & Sons, New York, N.Y., 1998, which is hereby incorporated by reference. It is to be understood that stringency conditions, including conditions of high stringency, vary according to the probe/primer and target sequences and that a person of ordinary skill in the art is readily able to determine such conditions using routine techniques. Substantially identical sequences include sequences that hybridize under high stringency conditions to one or more of SEQ ID NOs: 1-20 or to a complement thereof.

In alternative embodiments, miR-223 molecules include, without limitation, the miR-223 molecules described herein (e.g., SEQ ID NOs: 1-20) and fragments and variants and modifications thereof, for example, those that have an improved property e.g., biological or physiochemical or pharmaceutical properties, when compared to the starting species. An "improved" property includes, without limitation, promotion of differentiation, or inhibition or decrease of self-renewal or inhibition, or decrease of engraftment, of a leukemic cell, such as a LSC or LPC, or treatment of a myeloid leukemia, improved stability in a pharmaceutical formulation and in a patient, etc.

A "fragment" of a miR-223 molecule may be about 5, 6, 7, 8, 9, 10, 11, 12, 13, 14, 15, 16, 17, 18, 19, 20, 21, 22, 23, 24 or 25 nucleotides, or at least 30, 35, 40, 45, or 50 nucleotides, or at least 55, 60, 65, 70, 75, 80, 85, 90, 95, 100, 105, 110, 115 or 120 nucleotides in length, or any integer value therebetween. A fragment of a miR-223 precursor molecule may include a corresponding mature or star sequence. A fragment of a mature or star miR-223 molecule may include a seed sequence e.g., a sequence including positions 2-7 of a mature or star miR-223 molecule.

A "variant" miR-223 molecule includes a molecule that has less than 100% nucleotide identity to a wild type miR-223 molecule as exemplified herein or known in the art. A "variant" miR-223 molecule also includes miR-223 molecules from different species, or miR-223 molecules containing one or more nucleotide substitutions, deletions or insertions. In alternative embodiments, a miR-223 molecule may be nuclease resistant by for example incorporation of a ribonucleotide modified into the 2'-position. Exemplary 2'-modified ribonucleotides include those modified at the 2' position with fluoro, amino, alkyl, alkoxy, and O-allyl.

In alternative embodiments, "variant" miR-223 molecule also includes miR-223 molecules having modifications including, but are not limited to, replacement of the phosphate groups/phosphodiester linkages on the oligonucleotide backbone, replacement of phosphate and/or hydroxyl groups on the nucleotide at the 5'-terminus of the oligonucleotide or modifications of the sugar (ribose) moieties with various groups including but not limited to 2 O-Me substitutions. One example of a variant RNA is phosphorothioate RNA.

A miR-223 molecule is "substantially pure" or "isolated" when it is separated from the components that naturally accompany it. Typically, a miR-223 molecule is substantially pure when it is at least 10%, 20%, 30%, 40%, 50%, or 60%, more generally 70%, 75%, 80%, or 85%, or over 90%, 95%, or 99% by weight, of the total material in a sample. Thus, for example, a miR-223 molecule that is chemically synthesised, produced by recombinant technology, or isolated by known purification techniques, will be generally be substantially free from its naturally associated components. A substantially pure miR-223 molecule therefore can be obtained, for example, by extraction from a natural source; by expression of a recombinant nucleic acid molecule encoding the miR-223 molecule; or by chemical synthesis. For example, a mature miR-223 molecule or a miR-223* molecule may be isolated by processing of a miR-223 precursor molecule or by direct chemical synthesis or recombinant techniques. Purity can be measured using any appropriate method such as column chromatography, gel electrophoresis, HPLC, etc. A miR-223 molecule is substantially pure or "isolated" when it is not immediately contiguous with (i.e., covalently linked to) the nucleotide sequences with which it is normally contiguous in the naturally occurring genome of the organism from which it is derived. In vivo and in vitro processed products of miR-223 precursor molecules are also encompassed by an "isolated" miR-223 molecule. Preferably, an isolated miR-223 molecule comprises at least about 40%, 50%, 60%, 70%, 80%, 90%, 95%, or 99% (on a molar basis) of all macromolecular species present. Thus, an isolated gene or nucleic acid molecule can include a gene or nucleic acid molecule which is synthesized chemically or by recombinant means. A miR-223 molecule contained in a vector is included in the definition of "isolated" as used herein.

MiR-223 molecules, including fragments and variants, may be assayed for efficacy in promoting differentiation, inhibiting or decreasing self-renewal or of engraftment, of a leukemic cell such as a leukemic stem cell using methods described herein or known in the art. In alternative embodiments, miR-223 molecules may be assayed for their effect on apoptosis on leukemic cells such as leukemic stem cells (e.g., by Annexin V staining, alterations in cell cycle by e.g., BrdU assay), differentiation assays, FACs analysis, etc.

MiR-223 molecules may also be used in screening test compounds for treating a myeloid leukemia, or for promoting differentiation of a leukemic cell e.g., LSC or LPC. Candidate compounds may be identified using a variety of techniques, including screening of combinatorial libraries or using predictive software. In general, test compounds are identified from large libraries of both natural products or synthetic (or semi-synthetic) extracts or chemical libraries according to methods known in the art. Those skilled in the field of drug discovery and development will understand that the precise source of test extracts or compounds is not critical to the method(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available. Alternatively, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, Fla., USA), and PharmaMar, Mass., USA. Furthermore, if desired, any library or compound is readily modified using standard chemical, physical, or biochemical methods.

Candidate compounds may be identified based upon comparison with MiR-223 molecules with respect to the ability of a test compound in promoting differentiation, inhibiting or decreasing self-renewal or of engraftment, of a leukemic cell such as a leukemic stem cell using routine methods available in the art. Identified candidate compounds may be subsequently evaluated for their ability to treat a myeloid leukemia e.g. AML or CML. In one embodiment, when a crude extract is found to treat myeloid leukemia or exhibit efficacy in promoting differentiation, inhibiting or decreasing self-renewal or of engraftment, of a leukemic cell, further fractionation of the positive lead extract is necessary to isolate chemical constituents responsible for the observed effect. Thus, the goal of the extraction, fractionation, and purification process is the careful characterization and identification of a chemical entity within the crude extract having the desired activities. The same assays described herein for the detection of activities in mixtures of compounds can be used to purify the active component and to test derivatives thereof. Methods of fractionation and purification of such heterogeneous extracts are known in the art. If desired, compounds shown to be useful agents for treatment are chemically modified according to methods known in the art. Compounds identified as being of therapeutic, prophylactic, or other value may be subsequently analyzed using a AML or CML animal model, or any other animal model suitable for myeloid leukemia.

Therapies, Pharmaceutical Compositions, Dosages, and Administration

MiR-223 molecules may be administered to a subject to treat a myeloid leukemia, such as AML or CML. In alternative embodiments, the myeloid leukemia is a leukemia that is resistant to treatment with an exogenous differentiating agent i.e., an agent that, when added to a cell in vitro or in vivo, promotes the differentiation of the cell. For example, the myeloid leukemia may be an AML that is resistant to treatment with a known differentiating agent, such as a retinoic acid (e.g., ATRA) or a cytokine (e.g., G-CSF or GM-CSF). By "resistant to a differentiating agent" is meant that the leukemia does not substantially respond to treatment with the differentiating agent or that a leukemic cell does not undergo differentiation when contacted with the differentiating agent. Identification of such resistant leukemias and leukemic cells is known in the art.

In alternative embodiments, the AML is CD33+ AML, AML with FLT3 mutations, AML with CKIT mutations, or AML with MLL partial tandem duplications. In some embodiments, a miR-223 molecule may be used to treat subjects who have failed (relapsed) after standard chemotherapy or bone marrow transplantation or other emerging or novel targeted therapies. By "treat," "treatment" or "treating" is meant ameliorating symptoms associated with a myeloid leukemia such as AML or CML, including preventing or delaying the onset of the disease symptoms and/or lessening the severity or frequency of the disease symptoms and/or prolonging remission and/or decreasing the frequency or severity of relapse. In alternative embodiments, treating includes promoting differentiation, or inhibiting or decreasing self-renewal, or inhibiting or decreasing engraftment, in a leukemic cell, such as an LSC or an LPC.

In alternative embodiments, miR-223 molecules may be used ex-vivo to remove or eliminate leukemic stem cells (e.g., CD34+, CD38−) from the bone marrow of a subject prior to re-infusion back into the subject. As used herein, a subject may be a human, non-human primate, rat, mouse, cow, horse, pig, sheep, goat, dog, cat, etc. The subject may be a clinical patient, a clinical trial volunteer, a pediatric patient, an adult patient, an experimental animal, etc. The subject may be suspected of having or at risk for a myeloid leukemia, be diagnosed with a myeloid leukemia, or be a control subject that is confirmed to not have a myeloid leukemia. Diagnostic methods for myeloid leukemias and the clinical delineation of myeloid leukemias are known to those of ordinary skill in the art.

MiR-223 molecules may be provided alone or in combination with other compounds (for example, chemotherapeutics), in the presence of a liposome, an adjuvant, or any pharmaceutically acceptable carrier, in a form suitable for administration to mammals, for example, humans, cattle, sheep, etc. If desired, treatment with a miR-223 molecule according to the invention may be combined with traditional and existing, or emerging, therapies for AML, such as cytarabine in combination with an anthracycline, FLT3 inhibitors or anti-CD33 antibodies.

MiR-223 molecules may be provided chronically or intermittently. "Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature. In alternative embodiments, miR-223 molecules are administered to a subject in need of such inhibitors, e.g., a subject diagnosed with or suspected of having a myeloid leukemia, such as CML or AML. In alternative embodiments, the AML is a non-APL AML. In alternative embodiments, the AML is resistant to a differentiating agent, such as a retinoic acid (e.g., ATRA) or a cytokine.

In alternative embodiments, a miR-223 molecule may be effectively delivered to leukemic cells, e.g., LSC, by a variety of methods known to those skilled in the art. Such methods include but are not limited to liposomal encapsulation/delivery, vector-based gene transfer, fusion to peptide or immunoglobulin sequences for enhanced cell targeting and other techniques. Suitable viral vectors include retroviral vectors such as lentiviral vectors, adenovirus vectors, adeno-associated virus vectors, etc. In alternative embodiments, a miR-223 molecule, may also be formulated in pharmaceutical compositions well known to those in the field. These include liposomal formulations and combinations with other agents or vehicles/excipients such as cyclodextrins which may enhance delivery of the miRNA. In alternative embodiments, suitable carriers include lipid-based carriers such as a stabilized nucleic acid-lipid particle (e.g., SNALP or SPLP), cationic lipid or liposome nucleic acid complexes (i.e., lipoplexes), a liposome, a micelle, a virosome, or a mixture thereof. In other embodiments, the carrier system is a polymer-based carrier system such as a cationic polymer-nucleic acid complex (i.e., polyplex). In alternative embodiments, the carrier system is a cyclodextrin-based carrier system such as a cyclodextrin polymer-nucleic acid complex. In further embodiments, the carrier system is a protein-based carrier system such as a cationic peptide-nucleic acid complex.

Suitable carriers are known in the art and are described in, without limitation, United States Patent Application Nos. 20070173476 published Jul. 26, 2007; 20050008617 published Jan. 13, 2005; 20050014962 published Jan. 20, 2005; 20050064595 published Mar. 24, 2005; 20060008910 published Jan. 12, 2006; 20060051405 published Mar. 9, 2006; 20060083780 published Apr. 20, 2006; 20050008689 published Jan. 13, 2005; 20070172950 published Jul. 26, 2007; U.S. Pat. Nos. 7,101,995 issued Sep. 5, 2006 to Lewis, et al.; 7,220,400 issued May 22, 2007, to Monahan, et al.; 5,705,385 issued Jan. 6, 1998 to Bally, et al.; 5,965,542 issued Oct. 12, 1999 to Wasan, et al.; 6,287,591 issued Sep. 11, 2001 to Semple, et al., all of which are hereby incorporated by reference.

In one embodiment, the present invention contemplates a nucleic acid-lipid particle comprising a miR-223 molecule. In addition to the references described above, suitable nucleic acid-lipid particles and their use are described in U.S. Pat. Nos. 6,815,432, 6,586,410, and 6,534,484.

Conventional pharmaceutical practice may be employed to provide suitable formulations or compositions to administer the miR-223 molecules to subjects suffering from, at risk of, or presymptomatic for a myeloid leukemia such as CML or AML. Suitable pharmaceutical compositions may be formulated by means known in the art and their mode of administration and dose determined by the skilled practitioner. Any appropriate route of administration may be employed, for example, parenteral, intravenous, subcutaneous, intramuscular, intracranial, intraorbital, ophthalmic, intraventricular, intracapsular, intraspinal, intrathecal, intracisternal, intraperitoneal, intranasal, aerosol, lavage, topical, oral administration, or any mode suitable for the selected treatment. Therapeutic formulations may be in the form of liquid solutions or suspensions. For enteral administration, the compound may be administered in a tablet, capsule or dissolved in liquid form. The tablet or capsule may be enteric coated, or in a formulation for sustained release. For intranasal formulations, in the form of powders, nasal drops, or aerosols. For parenteral administration, a miR-223 molecule may be dissolved in sterile water or saline or a pharmaceutically acceptable vehicle used for administration of non-water soluble miR-223 molecules such as those used for vitamin K. Suitable formulations include those that have desirable pharmaceutical properties, such as targeted delivery to leukemic cells, improved serum half-life/ stability of a miR-223 molecule, improved intracellular penetration and cytoplasmic delivery, improved persistence of in-vivo activity, reduction in dose required for efficacy, reduction in required dosing frequency, etc. In alternative embodiments, a liposomal nanoparticle-based dosing formulation of a miR-223 molecule may be prepared using methods well known to those skilled in the art and currently practiced for the preparation pharmaceutical formulations of other oligonucleotide-based reagents/therapeutics including anti-sense oligonucleotides and/or RNAi (siRNA)-based agents.[10-13] In alternative embodiments, a gene therapy approach for transduction of miR-223 molecules to target cells (e.g. CD34+ CD38– cells or leukemic stem cells) using for example lentiviral-based vectors, may be used.

Methods well known in the art for making formulations are found in, for example, *Remington: the Science & Practice of Pharmacy* by Alfonso Gennaro, 20$^{th}$ ed., Williams & Wilkins, (2000). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. For therapeutic or prophylactic compositions, the miR-223 molecules are administered to an individual in an amount sufficient to stop or slow a myeloid leukemia such as CML or AML, or to promote differentiation, or inhibit or decrease self-renewal, or inhibit or decrease engraftment of myeloid leukemic cells. Suitable formulations may be provided in a kit including one or more miR-223 molecule, together with instructions for using the miR-223 molecule to treat a myeloid leukemia. The kit may contain additional agents such as a pharmaceutical carrier e.g, a liposomal carrier or additional active ingredients such as a chemotherapeutic agent. The additional agents may be provided in the same container as that containing the miR-233 molecule or may be provided in a container separate from that containing the miR-233 molecule.

An "effective amount" of a miR-223 molecule according to the invention includes a therapeutically effective amount or a prophylactically effective amount. A "therapeutically effective amount" refers to an amount effective, at dosages and for periods of time necessary, to achieve the desired therapeutic result, such as treatment of a myeloid leukemia or promotion of differentiation, or inhibition or decrease of self-renewal or inhibition or decrease of engraftment, of a leukemic cell, such as an LSC. The increase or decrease may be between 10% and 90%, e.g., 10%, 20%, 30%, 40%, 50%, 60%, 70%, 80%, 90%, or may be over 100%, such as 200%, 300%, 500% or more, when compared with a control or reference subject, sample or compound.

A therapeutically effective amount of a miR-223 molecule may vary according to factors such as the disease state, age, sex, and weight of the individual subject, and the ability of the miR-223 molecule to elicit a desired response in the individual. Dosage regimens may be adjusted to provide the optimum therapeutic response. A therapeutically effective amount is also one in which any toxic or detrimental effects of the miR-223 molecule are outweighed by the therapeutically beneficial effects. A "prophylactically effective amount" refers to an amount effective, at dosages and for periods of time necessary, to achieve the desired prophylactic result, such as prevention or protection against a myeloid leukemia or promotion of differentiation, inhibition or decrease of self-renewal or inhibition or decrease of engraftment of leukemic cells, such as leukemic stem cells. Typically, a prophylactic dose is used in subjects prior to or at an earlier stage of disease, so that a prophylactically effective amount may be less than a therapeutically effective amount. In alternative embodiments, dosages may be adjusted depending on whether the subject is in remission from a myeloid leukemia or not. A preferred range for therapeutically or prophylactically effective amounts of a miR-223 molecule may be any integer from 0.1 nM-0.1M, 0.1 nM-0.05M, 0.05 nM-15 µM or 0.01 nM-10 µM. In alternative embodiments, a therapeutically or prophylactically effective amount that is administered to a subject may range from about 5 to about 3000 micrograms/kg if body weight of the subject, or any number therebetween.

In alternative embodiments, the miR-223 molecule is provided in an amount that is from 10% to 99% greater than the amount present in leukemic cells, or more generally at least 10%, 20%, 30%, 40%, 50, 55% or 60%, or at least 65%, 75%, 80%, 85%, 90%, or 95%, or as much as 96%, 97%, 98%, or 99% greater than the amount present in leukemic cells. In alternative embodiments, the miR-223 molecule is provided in an amount that is 0.5 to 50 fold greater than the amount present in leukemic cells, or more generally at least 0.5, 1, 1.5, 2, 5, 10, 20, 25, 30, 35, 40, 45 fold greater than the amount present in leukemic cells. In alternative embodiments, the miR-223 molecule is provided in an amount that is equivalent to the amount present in non-leukemic stem cells or the amount present in normal myeloid cells. In alternative embodiments, administration of a miR-223 molecule to a subject, leads to a decrease of leukemic cells in the subject by 10% to 99%, or more generally by at least 10%, 20%, 30%, 40%, 50, 55% or 60%, or at least 65%, 75%, 80%, 85%, 90%, or 95%, or at least 96%, 97%, 98%, 99%, or 100%; or by 0.5 to 50 fold, or more generally at least 0.5, 1, 1.5, 2, 5, 10, 20, 25, 30, 35, 40, 45, 50, 60, 70, 80, 90 or 100 fold or more, when compared to a control or reference.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

The present invention will be further illustrated in the following examples.

EXAMPLE 1 miR-223 can Decrease the Leukemic Activity of Murine Leukemia Models

Two independent and clinically relevant acute myeloid leukemia models driven by MN1 and NUP98–HOXD13 (ND13)+Meis1[14-17] were used to investigate the anti-leukemic activity of miR-223.

A retroviral vector system was used to over-express pre-miR-223[5], including the precursor transcript of miR-223 with about 40 bp of flanking genomic region (Chen et al., 2004), in the MN1 and ND13+Meis1 cell lines using the empty vector (MDH-1) as control (ctl).

For all in vivo studies a murine transplantation model was used[14]. The in vitro assays included growth curves, colony forming assays (CFCs), FACS, and differentiation assays. Briefly, we cultured MN1 as well as ND13+Meis1 cells on feeder cells producing miR-223 retrovirus. Then, the infected cells were sorted for GFP positive cells, expanded in vitro and transplanted into mice. Every four weeks tail vein bleeds were performed and the percentage of GFP+ cells assessed. MN1 cells were plated for CFC assays in methylcellulose and their colony-forming potential measured by colony counts and serial replating. Growth curves: GFP sorted cells were seeded with the same amount in well plates and every day the amount of cells counted.

Figure 4:
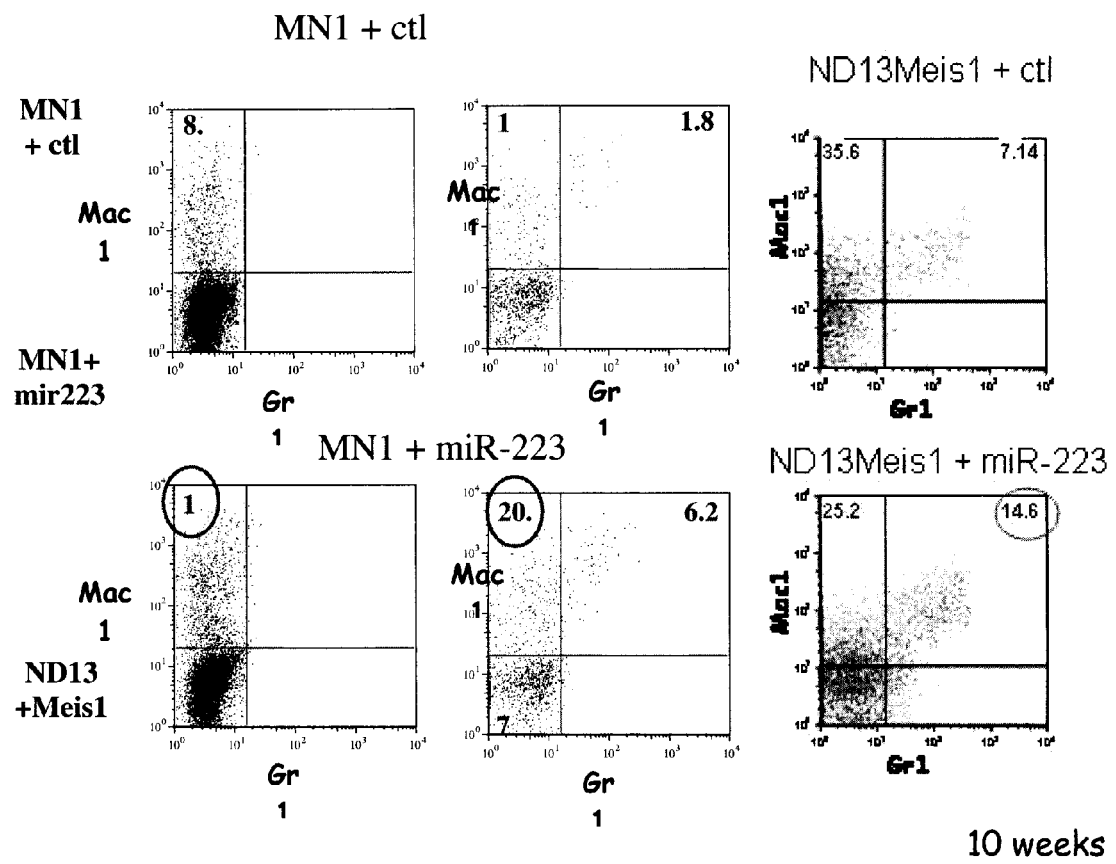
FIG. 4 shows the differentiation-inducing activity of pre-miR-223 in the MN1 and ND13+Meis1 models of leukemia in vitro. Overexpression of pre-mir-223 in 2 independent experiments led to an in vitro increase of the myeloid differentiation marker Mac1 in MN1 leukemia cells. Overexpression of pre-miR-223 in ND13+Meis1 cells led to an increase of Mac1/Gr1 double positive cells, demonstrating the differentiation potential of pre-miR-223.
Figure 5:
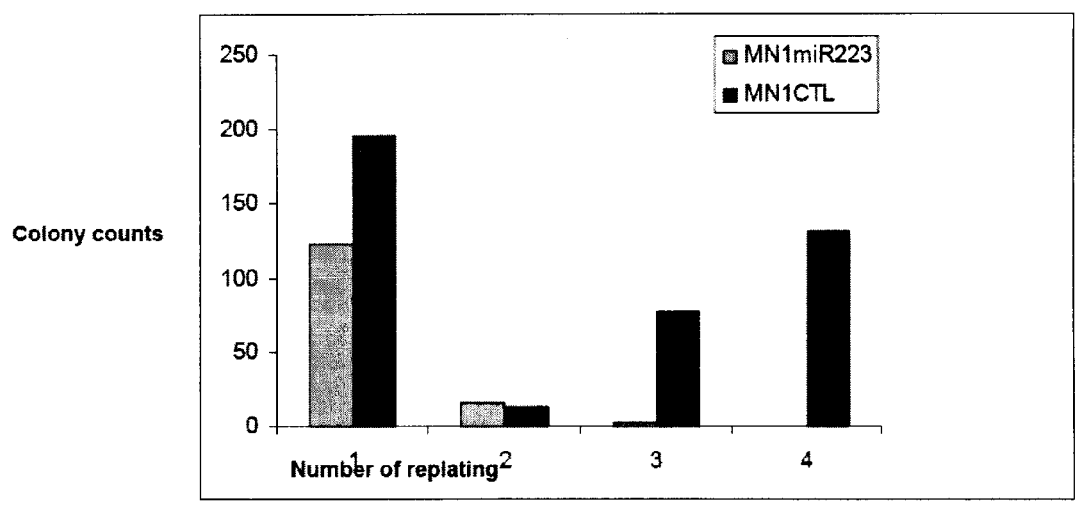
FIGS. 5A-B show colony forming cell (CFC) and proliferation assays in MN1+cells. A. Reduced replating capacity of MN1+mir223 cells compared to MN1ctl cells demonstrated by a lower number of progenitor cells in MN1 cells over expressing miR-223. After the $1^{st}$ round of CFC replating, the replating capacity dramatically decreases in MN1 cells expressing miR-223, indicating a lower number of progenitor cells. B. Decreased proliferation in MN1+ cells expressing miR-223, compared to the control.
Figure 5:
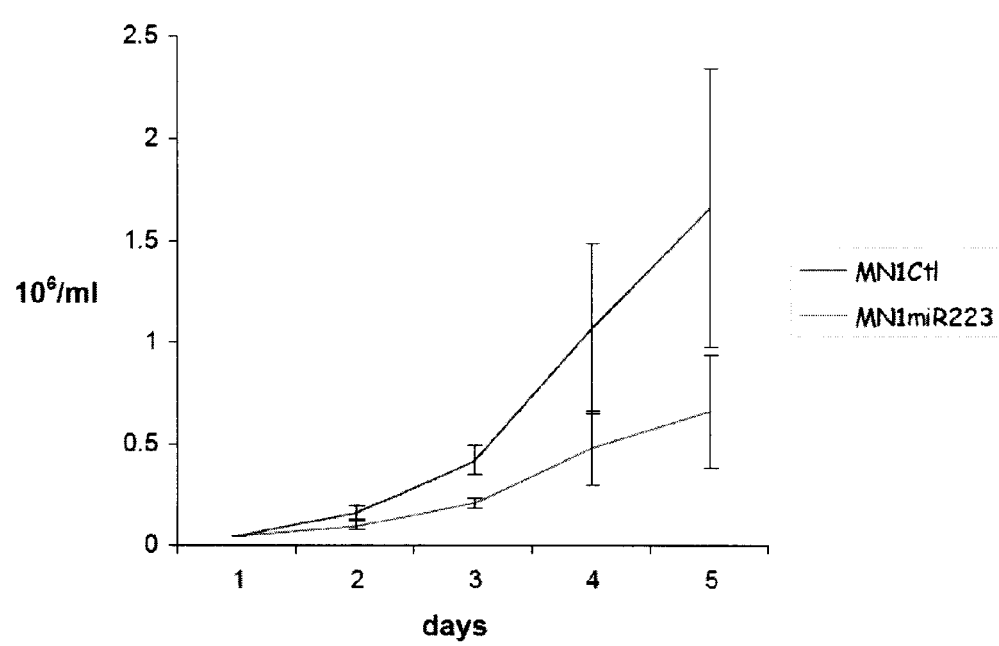

In the MN1 model, decreased proliferation of MN1+miR-223 cells compared to MN1+MDH1 cells, as well as a decreased CFC replating capacity after the $3^{rd}$ replating, was observed (FIGS. 5A-B). Furthermore, FACS data demonstrated that MN1+miR223 display an increased number of Mac1+ cells (macrophage marker) (FIG. 4). By contrast, assays directed to determining whether MN1+mir-223 cells display an increased sensitivity towards differentiating cytokines like G-CSF and GM-CSF did not show any difference under the conditions used in these assays.

Mice injected with $2\times10^5$ sorted MN1+miR-223 cells in independent studies showed decreased and ultimately completely diminished engraftment. With respect to survival, in the first experiment, all control mice died (3/3 or 7/7), whereas all MN1+mir223 mice were still alive (0/3 or 0/5) after 90 or 180 days. Considering a mean survival time of 30-50 days for MN1 leukemias, this result is significant. A second independent experiment with newly infected cells and a cell dose of $5\times10^5$/mouse confirmed the results of the first experiment. After 4 weeks the MN1+miR223 mice showed an engraftment of <1%, compared to 25% in the MN1+MDH1 control mice.

In the ND13Meis1 cell model, mice injected with $5\times10^5$ sorted ND13Meis1+miR-223 cell line cells showed decreased and ultimately completely diminished engraftment. With respect to survival, in the first experiment all control mice died (3/3 or 6/6), whereas 2/ or 4/5 ND13Meis1+mir223 mice were still alive (2/3) after 90 or 180 days. Considering a mean survival time of 40-60 days for ND13meis1 leukemias, this result is significant. Regular weekly bleeds revealed unique engraftment kinetics in the ND13Meis1+mir-223 mice, with a steadily decreasing engraftment not only in the ND13Meis1+mir-233 compartment (GFP/YFP double positive cells), but also in the ND13Meis1 (YFP only) compartment, indicating a possible interaction between the cells. Thus, from an initial engraftment (4 weeks) in ND13Meis1+miR-223 cells ranging from 1-10% double positive cells (GFP/YFP, ND13Meil+mir-223) and 1-8% single positive cells (YFP, ND13Meis1 only), after 8 weeks the engraftment of both compartments diminished to <1% GFP/YFP and YFP positive cells, respectively. The engraftment kinetics showed miR-223 mice: between 1-10% double positive mice→ engraftment diminishes, after 8 weeks: <1% double-positive cells. In conclusion, by overexpressing miR-223 we observed a decrease in the leukemic potential of MN1 and ND13+Meis1 leukemia cells. In vitro experiments indicated an increased differentiation ability of the leukemic expressing miR-223 cells.

Figure 3:
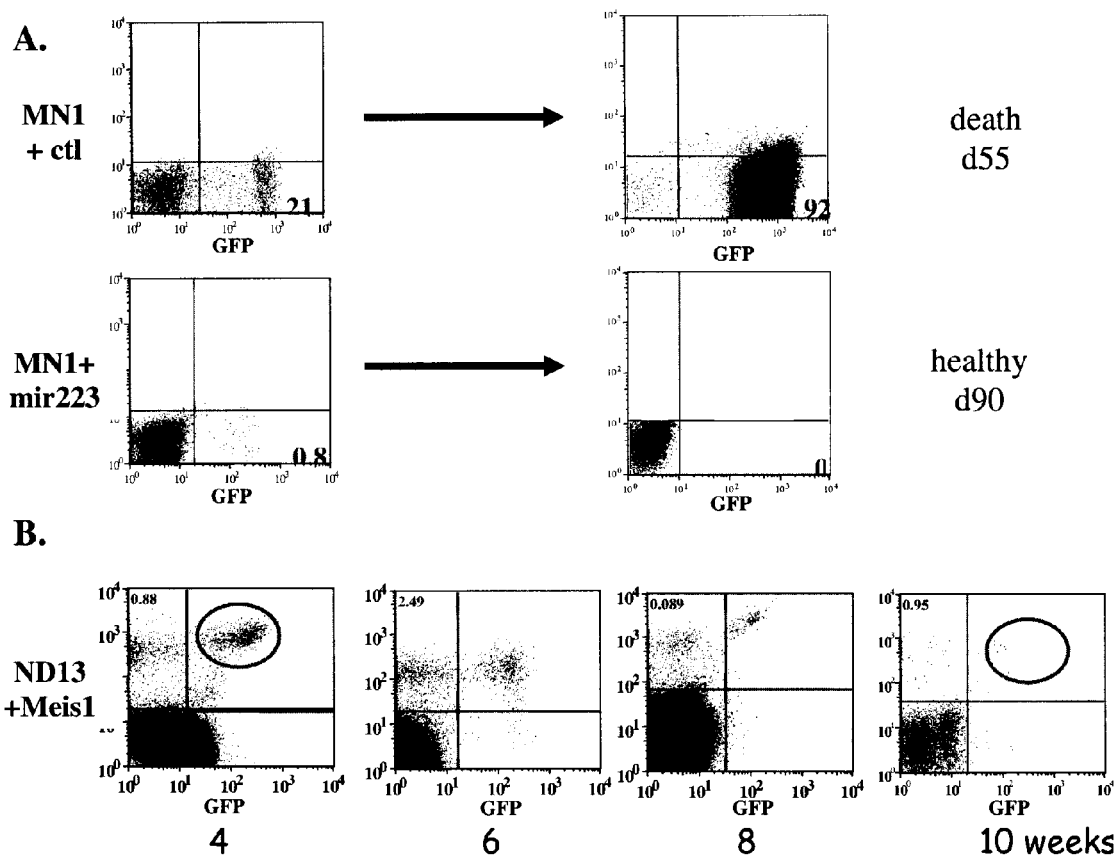
FIGS. 3A-C show engraftment kinetics of MN1±miR-223 and ND13+Meis1+miR-223 mice. A. MN1±miR-223 mice after 4 weeks until death or d90. B. ND13+Meis1+miR-223 as marked in the GFP/YFP double positive compartment after 4, 6, 8 and 10 weeks. C. MN1±miR-223 and ND13+Meis1+miR-223 mice after 4 weeks until death or d90. Engraftment is monitored by the level of GFP (MN1) or GFP/YFP positive (ND13+Meis1) cells in the peripheral blood. The double positive cells diminish over time.
Figure 3:
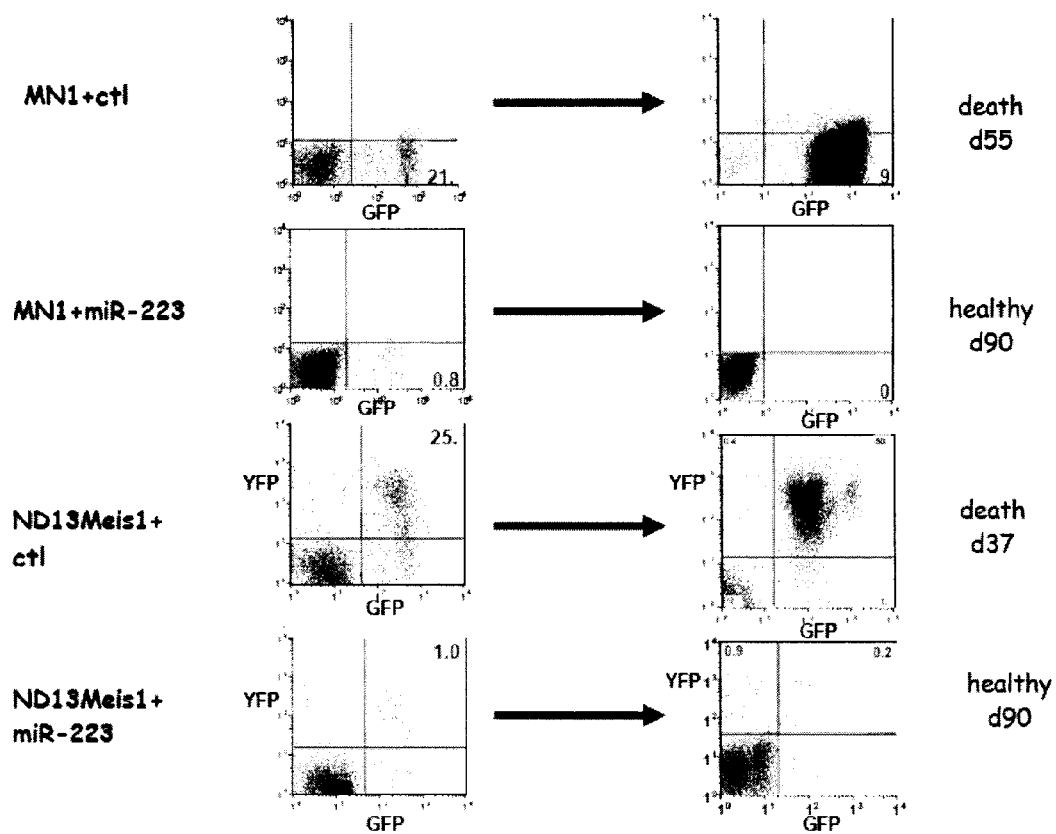

Accordingly, independent in vivo assays demonstrated that over-expression of pre-miR-223 in MN1 cells as well as in a ND13+Meis1 leukemia cell line led to reduced engraftment and survival of the test animals by a complete disappearance of the leukemic cells (FIGS. 3, 4).

In contrast, all the control mice died within 30-50 days of the expected leukemia. This is remarkable, considering that MN1 and ND13+Meis1 are two independent models of a highly aggressive leukemia.

In vitro experiments demonstrated increased differentiation of MN1 and ND13+Meis1 cells with miR-223 overexpression, indicating that pre-miR-223 circumvents the block in differentiation and thus causes maturation of leukemic cells. In line with this, MN1 cells expressing pre-miR-223 lose their infinite replating capacity in CFC assays compared to the control, demonstrating a loss of immortalized long-term replating progenitor cells.

These results demonstrate that overexpression of pre-miR-223 forces leukemic cells to differentiate in vitro and in vivo, and therefore that increased levels of miR-223 can overcome the differentiation block in leukemic cells.

EXAMPLE 2

Figure 1B:
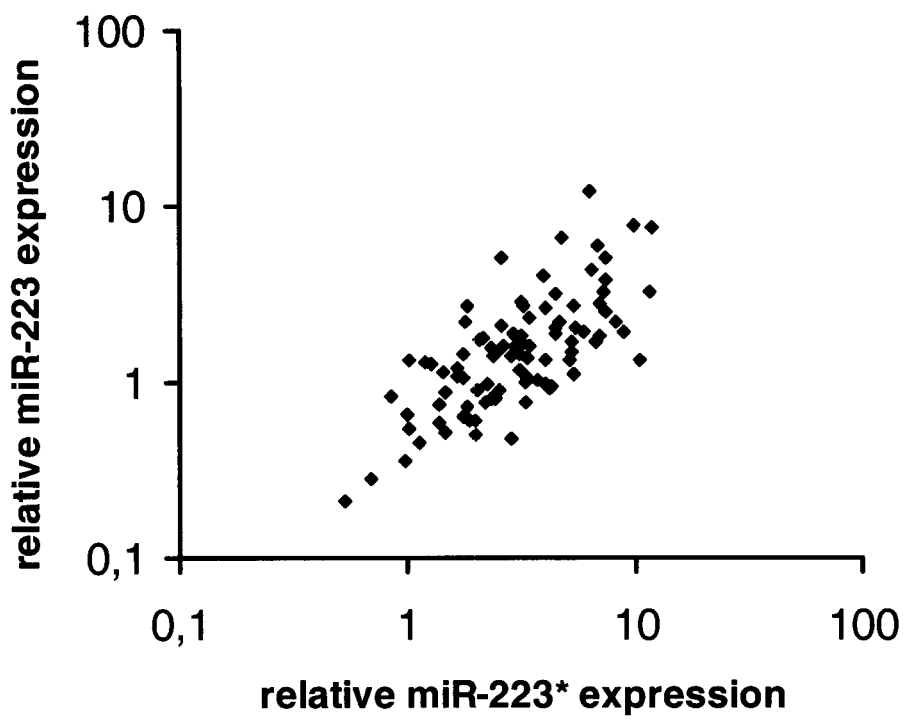
FIG. 1B shows a correlation of mature miR-223 and miR-223* expression in >100 patient samples.
Figure 2:
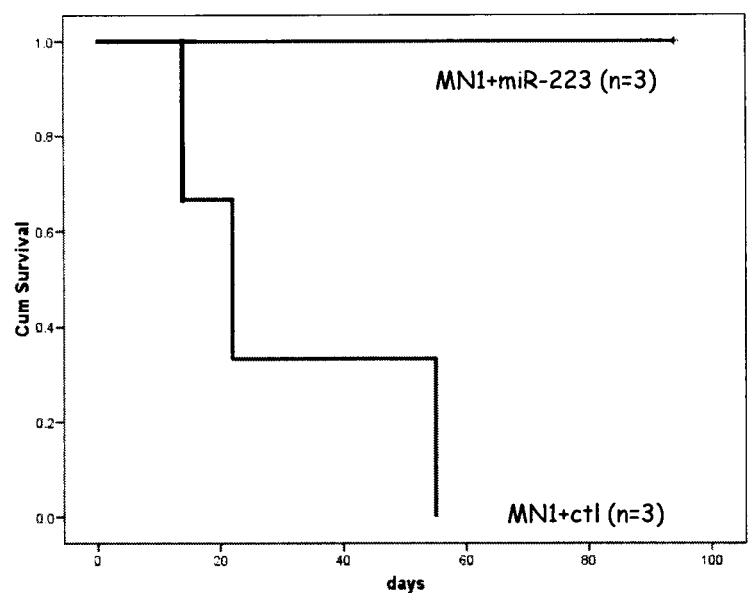
FIGS. 2A-D show survival curves of MN1±miR-223 (A-B) and ND13+Meis1±miR-223 (C-D). Mice that received the control (ctl) vector died of leukemia, whereas mice in the miR-223 arm survived.
Figure 2:
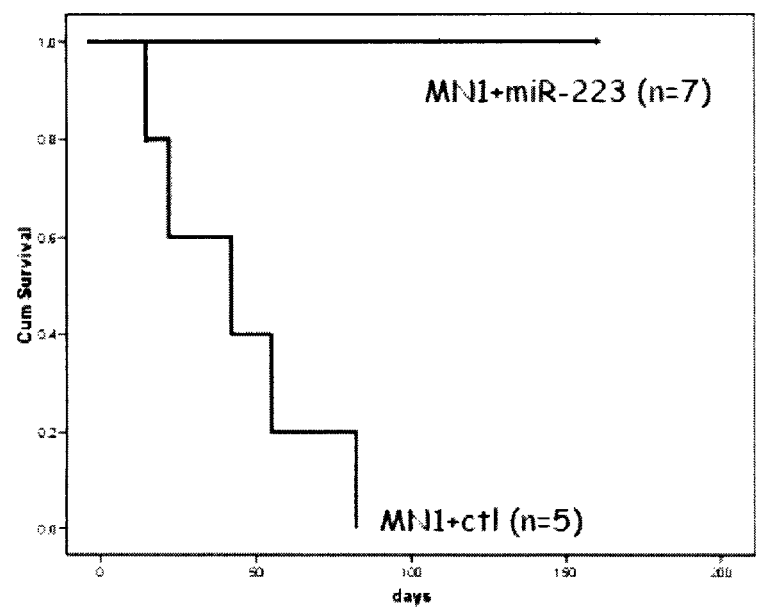
Figure 2:
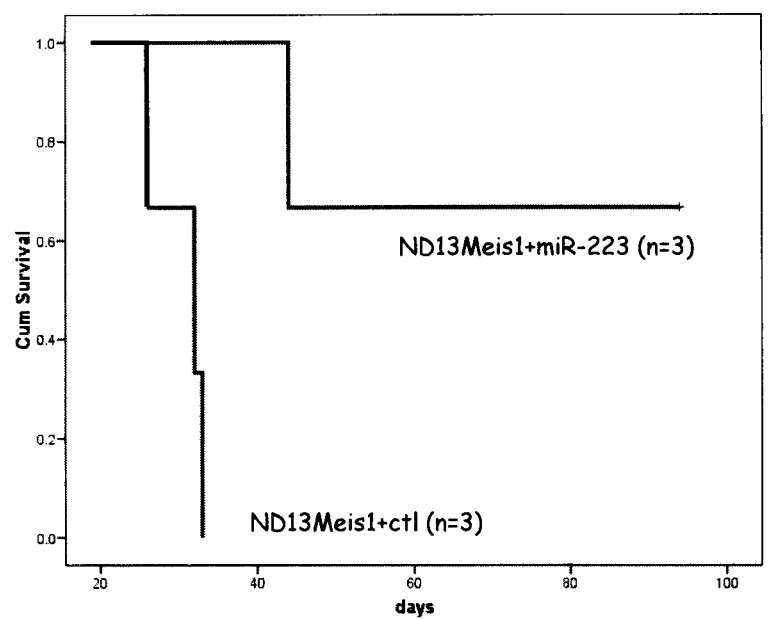
Figure 2:
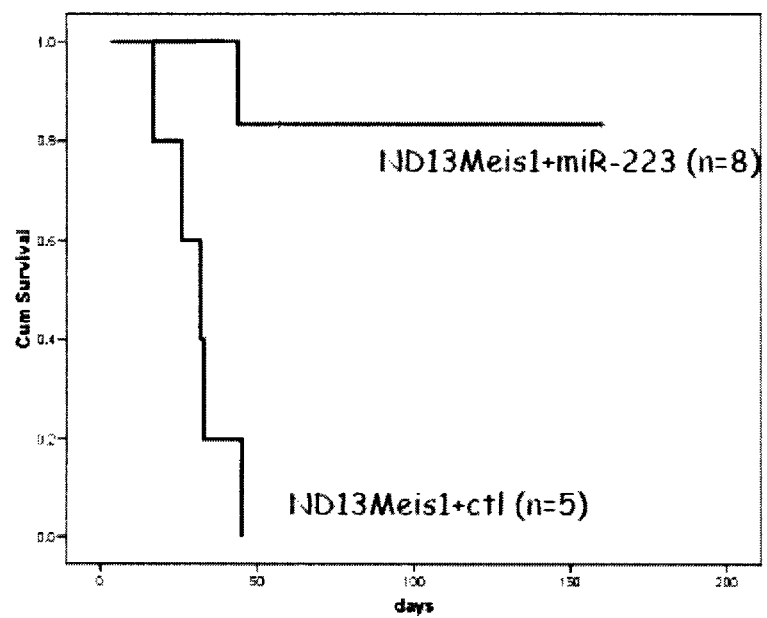

Expression profiling of miR-223 and miR-223star in human AML patient samples MiRNA expression profiling of sorted AML patient samples (FIG. 1A) revealed that miR-223 has lower expression levels in undifferentiated leukemia cell populations that comprise the leukemic stem cells. MiR-223 is relatively poorly expressed within the leukemic stem cell fraction compared to the bulk leukemic cells as demonstrated in FIG. 1A. Further, we could show by sequencing that miR-223 star expression levels can not only exceed, but also be highly differentially expressed in the myeloid progenitor ND13 cells and is drastically downregulated in the leukemic ND13+Meis1 cells. Expression profiling of miR-223 and miR-223star in human AML patient samples showed high expression of miR-223star and a correlation of miR-223star and miR-223 expression (FIG. 1B).

More specifically, expression profiling of miR-223 expression in AML patient samples revealed a significant negative correlation (p<0.05) with FLT3-ITDs, a negative prognostic marker for AML. Furthermore, expression profiling of sorted, subfractionated AML patient samples (n=5) revealed that miR-223 is significantly lower expressed (p<0.05) in the more primitive fraction (CD34+, CD38−) compared to the bulk population of AML cells. This together with our mouse in vivo data indicates that overexpression of miR-223 leads to loss of the self-renewal ability in LSC and to differentiation.

References

Aravin A, Tuschl T (2005) Identification and characterization of small RNAs involved in RNA silencing. FEBS Lett 579, 5830-5840

Bartel D P (2004) MicroRNAs: genomics, biogenesis, mechanism, and function. Cell 116, 281-297

Buechner T, Berdel W E, Schoch C, Haferlach T, Serve H L, Schnittger S, Kern W, Tchinda J, Reichle A, Staib P, Ludwig W D, Aul C, Sauerland M C, Heinecke A, Woermann B, Hiddemann W (2005) Treatment of AML in biological subgroups. Hematology 10 Suppl 1, 281-285

Chen C Z, Li L, Lodish H F, Bartel D P (2004) MicroRNAs modulate hematopoietic lineage differentiation. Science 303, 83-86

Costinean S, Zanesi N, Pekarsky Y, Tili E, Volinia S, Heerema N, Croce C M (2006) Pre-B cell proliferation and lymphoblastic leukemia/high-grade lymphoma in E(mu)-miR155 transgenic mice. Proc Natl Acad Sci USA 103, 7024-7029

Debernardi S, Skoulakis S, Molloy G, Chaplin T, Dixon-McIver A, Young B D (2007) MicroRNA miR-181a correlates with morphological sub-class of acute myeloid leukaemia and the expression of its target genes in global genome-wide analysis. Leukemia 21, 912-916

Fazi F, Rosa A, Fatica A, Gelmetti V, De Marchis M L, Nervi C, Bozzoni I (2005) A minicircuitry comprised of microRNA-223 and transcription factors NFI-A and C/EBPalpha regulates human granulopoiesis. Cell 123, 819-831

Fukao T, Fukuda Y, Kiga K, Sharif J, Hino K, Enomoto Y, Kawamura A, Nakamura K, Takeuchi T, Tanabe M (2007) An evolutionarily conserved mechanism for microRNA-223 expression revealed by microRNA gene profiling. Cell 129, 617-631

Gilliland D G, Jordan C T, Felix C A (2004) The molecular basis of leukemia. Hematology Am Soc Hematol Educ Program, 80-97

He L, Thomson J M, Hemann M T, Hernando-Monge E, Mu D, Goodson S, Powers S, Cordon-Cardo C, Lowe S W, Hannon G J, Hammond S M (2005) A microRNA polycistron as a potential human oncogene. Nature 435, 828-833

Heuser M, Argiropoulos B, Kuchenbauer F, Yung E, Piper J, Fung S, Schlenk R F, Dohner K, Hinrichsen T, Rudolph C, Schambach A, Baum C, Schlegelberger B, Dohner H, Ganser A, Humphries R K (2007) MN1 overexpression induces acute myeloid leukemia in mice and predicts ATRA resistance in AML patients. Blood 110(5):1639-47

Heuser M, Beutel G, Krauter J, Dohner K, von Neuhoff N, Schlegelberger B, Ganser A (2006) High meningioma 1 (MN1) expression as a predictor for poor outcome in acute myeloid leukemia with normal cytogenetics. Blood 108, 3898-3905

Hiddemann W, Kern W, Heinecke A, Sauerland C, Buchner T (2004) Priming with G-CSF in acute myeloid leukemia: preliminary data of the AMLCG. Ann Hematol 83 Suppl 1, S53-54

Hiddemann W, Spiekermann K, Buske C, Feuring-Buske M, Braess J, Haferlach T, Schoch C, Kern W, Schnittger S, Berdel W, Wormann B, Heinecke A, Sauerland C, Buchner T (2005) Towards a pathogenesis-oriented therapy of acute myeloid leukemia. Crit. Rev Oncol Hematol 56, 235-245

Kim V N (2005) MicroRNA biogenesis: coordinated cropping and dicing. Nat Rev Mol Cell Biol 6, 376-385

Koschmieder S, Rosenbauer F, Steidl U, Owens B M, Tenen D G (2005) Role of transcription factors C/EBPalpha and PU.1 in normal hematopoiesis and leukemia. Int J Hematol 81, 368-377

Kuchenbauer F, Schoch C, Kern W, Hiddemann W, Haferlach T, Schnittger S (2005) Impact of FLT3 mutations and promyelocytic leukaemia-breakpoint on clinical characteristics and prognosis in acute promyelocytic leukaemia. Br J Haematol 130, 196-202

Lewis B P, Burge C B, Bartel D P (2005) Conserved seed pairing, often flanked by adenosines, indicates that thousands of human genes are microRNA targets. Cell 120, 15-20

Ruby J G, Jan. C, Player C, Axtell M J, Lee W, Nusbaum C, Ge H, Bartel D P (2006) Large-scale sequencing reveals 21U-RNAs and additional microRNAs and endogenous siRNAs in *C. elegans*. Cell 127, 1193-1207

All citations are hereby incorporated by reference.

Other Embodiments

Although various embodiments of the invention are disclosed herein, many adaptations and modifications may be made within the spirit and scope of the invention in accordance with the common general knowledge of those skilled in this art. Such modifications include the substitution of known equivalents for any aspect of the invention in order to achieve the same result in substantially the same way. Accession numbers, as used herein, refer to Accession numbers from multiple databases, including GenBank, the European Molecular Biology Laboratory (EMBL), the DNA Database of Japan (DDBJ), or the Genome Sequence Data Base (GSDB), for nucleotide sequences, and including the Protein Information Resource (PIR), SWISSPROT, Protein Research Foundation (PRF), and Protein Data Bank (PDB) (sequences from solved structures), as well as from translations from annotated coding regions from nucleotide sequences in GenBank, EMBL, DDBJ, or RefSeq, for polypeptide sequences. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. All publications are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:

1. A method of treating a myeloid leukemia, or for promoting the differentiation of a leukemic stem cell that is resistant to a differentiating agent, the method comprising administering an effective amount of a miR-223 molecule to a subject in need thereof.

2. The method of claim 1 wherein the leukemia is a chronic myeloid leukemia (CML), an acute myeloid leukemia (AML), or is resistant to a differentiating agent.

3. The method of claim 1 wherein the differentiating agent is a retinoic acid or a cytokine.

4. The method of claim 3 wherein the retinoic acid is all-trans-retinoic acid (ATRA).

5. The method of claim 3 wherein the cytokine is granulocyte colony stimulating factor (G-CSF) or granulocyte macrophage colony stimulating factor (GM-CSF).

6. The method of claim 2 wherein the AML is a non-acute promyelocytic leukemia (non-APL AML) or is an ATRA-resistant APL.

7. The method of claim 1 wherein the miR-223 molecule comprises a sequence that is substantially identical to a sequence selected from one or more of SEQ ID NOs: 1-20.

8. The method of claim 1 wherein the treating comprises promoting differentiation in a leukemic 9. The method of claim 1 further comprising administering a chemotherapeutic agent or further comprising stem cell transplantation.

10. The method of claim 9 wherein the chemotherapeutic agent is administered or the stem cell transplantation is performed prior to or after administration of the miR-223 molecule.

11. The method of claim 1 wherein the miR-223 molecule is administered as part. of a consolidation or post-remission therapy.

12. The method of claim 1 wherein the subject has relapsed leukemia, is at a high risk for relapse, is over 60 years of age, is a poor candidate for chemotherapy, is a poor candidate for high dose chemotherapy, or is a poor candidate for stem cell transplantation.

13. The method of claim 1 wherein the subject is a human.

14. The method of claim 1 wherein the leukemic stem cell is a CML cell, an AML, cell, or a CD34+,CD38− cell.

* * * * *

SEQUENCE LISTING

```
<160> NUMBER OF SEQ ID NOS: 20

<210> SEQ ID NO 1
<211> LENGTH: 110
<212> TYPE: RNA
<213> ORGANISM: Homo sapiens

<400> SEQUENCE: 1
ccuggccucc ugcagugcca cgcuccgugu auuugacaag cugaguugga cacuccaugu      60
gguagagugu caguuuguca aauacccaa gugcggcaca ugcuuaccag                 110
```

```
<210> SEQ ID NO 2
<211> LENGTH: 22
<212> TYPE: RNA
<213> ORGANISM: Homo sapiens

<400> SEQUENCE: 2
ugucaguuug ucaaauaccc ca                                              22

<210> SEQ ID NO 3
<211> LENGTH: 22
<212> TYPE: RNA
<213> ORGANISM: Homo sapiens

<400> SEQUENCE: 3
cguguauuug acaagcugag uu                                              22

<210> SEQ ID NO 4

<400> SEQUENCE: 4

000

<210> SEQ ID NO 5

<400> SEQUENCE: 5

000

<210> SEQ ID NO 6
<211> LENGTH: 99
<212> TYPE: RNA
<213> ORGANISM: Danio rerio

<400> SEQUENCE: 6
cucuccuccu gaucuagacu cuucucuuag aguauuugac agacuguggu ugacacucga     60
ucuaaagggg ugucaguuug ucaaauaccc caagagagg                            99

<210> SEQ ID NO 7
<211> LENGTH: 89
<212> TYPE: RNA
<213> ORGANISM: Fugu rubripes

<400> SEQUENCE: 7
cacuuagugu auuugacaag cguucuuga cacucuuuau acgcgagugu caguuuguca      60 aauacccaa gugaggguguc acuugucug                                       89

<210> SEQ ID NO 8
<211> LENGTH: 85
<212> TYPE: RNA
<213> ORGANISM: Tetraodon nigroviridis

<400> SEQUENCE: 8
caggcccuuc acuuagugua uuugacaagc uguuugac acucuguauc ugcgagguguc     60 aguuugucaa auacccaag ugagg                                            85

<210> SEQ ID NO 9
<211> LENGTH: 86
<212> TYPE: RNA
<213> ORGANISM: Xenopus tropicalis

<400> SEQUENCE: 9
aguguggcac ugaguguauu ugacaagcug aguccgacac ucaaugagac agagugucag     60
``` uugucaaau accccaagug aggcac                                        86

<210> SEQ ID NO 10
<211> LENGTH: 100
<212> TYPE: RNA
<213> ORGANISM: Gallus gallus

<400> SEQUENCE: 10
cugcagugca gcacugcgug uauuugacaa gcugaguuug acacucaguc uggcagagug    60
ucaguuuguc aaauacccca agugaggcac uugcugagca                         100

<210> SEQ ID NO 11
<211> LENGTH: 111
<212> TYPE: RNA
<213> ORGANISM: Monodelphis domestica

<400> SEQUENCE: 11
ucuggcccag auccuucagu gccacacucc guguauuuga caagcugagu uggacacucc    60
gugucguaga gugucaguuu gucaaauacc ccaagugagg cauuugccua g            111

<210> SEQ ID NO 12
<211> LENGTH: 110
<212> TYPE: RNA
<213> ORGANISM: Mus Muscularis

<400> SEQUENCE: 12
ucuggccauc ugcagugauc cgcuccgugu auuugacaag cugaguugga cacucugugu   60
gguagagugu caguuuguca aauaccccaa guguggcuca ugccuaucag              110

<210> SEQ ID NO 13
<211> LENGTH: 110
<212> TYPE: RNA
<213> ORGANISM: Rattus norvegicus

<400> SEQUENCE: 13
ucuggccuuc ugcagguuua cgcuccgugu auuugacaag cugaguugga cacucugugu   60
gguagagugu caguuuguca aauaccccaa guguggcuca ugcuuaucag              110

<210> SEQ ID NO 14
<211> LENGTH: 110
<212> TYPE: RNA
<213> ORGANISM: Saguinus labiatus

<400> SEQUENCE: 14
ccuggccucc ugcagugcca cgcuccgugu auuugacaag cugaguugga cacuccgugu   60
gguagagugu caguuuguca aauaccccaa gugcgacaca ugcuuagcag              110

<210> SEQ ID NO 15
<211> LENGTH: 110
<212> TYPE: RNA
<213> ORGANISM: Macaca mulatta

<400> SEQUENCE: 15
cccggccucc ugcagugcca cgcuccgugu auuugacaag cugaguugga cacuccgugu   60
gguagagugu caguuuguca aauaccccaa gugcggcaua ugcuuaccag              110

<210> SEQ ID NO 16
<211> LENGTH: 110
<212> TYPE: RNA
<213> ORGANISM: Pongo pygmaeus

```
<400> SEQUENCE: 16
ccuggccucc ugcagugcca cgcuccgugu auuugacaag cugaguuaga cacuccgugu      60
gguagagugu caguuuguca aauacccaa gugcggcaca ugcuuaccag                110

<210> SEQ ID NO 17
<211> LENGTH: 110
<212> TYPE: RNA
<213> ORGANISM: Gorilla gorilla

<400> SEQUENCE: 17
ccuggccucc ugcagugcca cgcuccgugu auuugacaag cugaguugga cacuccaugu      60
gguagagugu caguuuguca aauacccaa gugcggcaca ugcuuaccag                110

<210> SEQ ID NO 18
<211> LENGTH: 110
<212> TYPE: RNA
<213> ORGANISM: Pan paniscus

<400> SEQUENCE: 18
ccuggccucc ugcagugcca cgcuccgugu auuugacaag cugaguugga cacuccaugu      60
gguagagugu caguuuguca aauacccaa gugcggcaca ugcuuaccag                110

<210> SEQ ID NO 19
<211> LENGTH: 110
<212> TYPE: RNA
<213> ORGANISM: Pan troglodytes

<400> SEQUENCE: 19
ccuggccucc ugcagugcca cgcuccgugu auuugacaag cugaguugga cacuccaugu      60
gguagagugu caguuuguca aauacccaa gugcggcaca ugcuuaccag                110

<210> SEQ ID NO 20
<211> LENGTH: 107
<212> TYPE: RNA
<213> ORGANISM: Artificial
<220> FEATURE:
<223> OTHER INFORMATION: Consensus sequence

<400> SEQUENCE: 20
cuggccuccu gcagugccac gcuccgugua uuugacaagc ugaguuggac acuccgugug      60
guagaguguc aguuugucaa auacccaag ugggcacaug cuuacag                  107
```